(12) United States Patent
Ball et al.

(10) Patent No.: US 6,869,780 B2
(45) Date of Patent: Mar. 22, 2005

(54) NODAVIRUS-LIKE DNA EXPRESSION VECTOR AND USES THEREFOR

(75) Inventors: Laurence A. Ball, Birmingham, AL (US); Kyle L. Johnson, Birmingham, AL (US); Karen N. Johnson, Birmingham, AL (US); B. Duane Price, Mountain Brook, AL (US)

(73) Assignee: The UAB Research Foundation, Birmingham, AL (US)

( * ) Notice: Subject to any disclaimer, the term of this patent is extended or adjusted under 35 U.S.C. 154(b) by 122 days.

(21) Appl. No.: 10/230,730

(22) Filed: Nov. 4, 2002

(65) Prior Publication Data

US 2003/0108863 A1 Jun. 12, 2003

Related U.S. Application Data

(62) Division of application No. 09/595,346, filed on Jun. 14, 2000, now Pat. No. 6,514,757.
(60) Provisional application No. 60/139,120, filed on Jun. 14, 1999, now abandoned.

(51) Int. Cl.[7] .................. C12N 15/86; C12N 15/63; C12N 15/64; C12N 5/10; C07H 21/02
(52) U.S. Cl. .................. 435/91.33; 435/320.1; 435/235.1; 435/69.1; 435/325; 435/348; 435/455; 435/456; 435/91.1; 435/91.31; 435/91.3; 435/91.32; 435/91.4; 536/23.1; 536/23.2; 536/23.5; 536/23.72; 536/24.1; 536/24.5

(58) Field of Search .................. 435/320.1, 235.1, 435/69.1, 325, 348, 69.6, 455, 456, 91.1, 91.31, 91.3, 91.32, 91.4, 91.33; 536/23.1, 23.2, 23.5, 23.72, 24.1, 24.5; 424/93.1, 93.2, 93.6

(56) References Cited

PUBLICATIONS

Ball, J. Virol., 1992, vol. 66, No. 4, pp. 2335–2345.*
Eckerle et al., Virology, 2002, vol. 296, pp. 165–176.*

* cited by examiner

*Primary Examiner*—David Guzo
(74) *Attorney, Agent, or Firm*—Benjamin Aaron Adler

(57) ABSTRACT

The present invention describes the production of a nodavirus-based DNA vector that drives abundant expression of foreign genes in a wide variety of cell types. The DNA plasmid is initially transcribed by a host-cell RNA polymerase to produce primary transcripts from which a nodaviral RNA-dependent RNA polymerase (RNA replicase) is translated. These primary transcripts are then amplified by the RNA replicase in an autonomous, cytoplasmic RNA replication. Such a vector is a useful addition to the current arsenal of expression vectors, and well suited to laboratory-scale and larger-scale expression of transcripts and/or proteins in eukaryotic cells.

28 Claims, 11 Drawing Sheets

SEQUENCE LISTING

```
<160> NUMBER OF SEQ ID NOS: 6

<210> SEQ ID NO 1
<211> LENGTH: 3204
<212> TYPE: DNA
<213> ORGANISM: Nodamura virus
<220> FEATURE:
<221> NAME/KEY: gene
<223> OTHER INFORMATION: cDNA of RNA1 genome segment

<400> SEQUENCE: 1
gtattgaatc caaaactcaa aatgctgaac tacgagacaa tcatcaacgg        50
cgcatcgagc gctctgaaca tcgtttcgcg tgcgttagga taccgcgtgc       100
cactagccaa atcgctggcg ctggtcgcgg ggtcctgcgt ggtgtacaaa       150
ataatcgtgc atcgacgcac gctcgtggcg ttcctggtaa tcggaccata       200
cgccacggtg gtgcagcacc gtctgccgat ggcccttcag agggccatca       250
ttgaatatac acgagaagac cgtgagatca gcctgtttcc gcaaaattcc       300
atcgtttccg cagaacacgc gcggaaagcg gataatgggc atccgatctc       350
cgggggaacg cgtgatgtcg cgagggagac tatttccctt gccataaggg       400
ccgctggttt tcgtcattac gaaatcagcc ccgcgaggca atcaccagct       450
gaggcggcaa gccaccaaca ttatgccgcc gctgacctcg tgagagcggc       500
tactgaagat aagatccaag acggtgatgt ggtagttgcc atcgacatcg       550
attactacct gcgtgacatt gaccgctacc tgggtcgtgg tgtcccgttc       600
```

| | |
|---|---|
| atggcttaca ccttcaatcc tgttgaagta gctggccgtg acggtgactc | 650 |
| cttttttccgg atcacgaaca atcaagtcac gtttgatgtt agtggcggtg | 700 |
| gatcttggtc ccatgaagtt tgggactggt gcgcgtttgg tgagttcatc | 750 |
| gagacccgag acgcgagctg gcttgcttgg ttcgcccggg cggttggact | 800 |
| caccaagtcg cagatccaca aagttcacta ctgccgtcca tggccgcaat | 850 |
| cgccccatcg cgctttggtg tggtgtctgc ctgtagcaag ctactggcgc | 900 |
| ttcactttca ttccgacgga cctgcatacg cgcacgcttc ggcgtgtgcg | 950 |
| ttatcaggac acgtcccggc ccggttggaa ttccatcgtc tcgaccgggt | 1000 |
| ccgaaggcct taatatcagc cttggtcgcg aaggagctga tcattgcgtg | 1050 |
| acgattccaa aggtgcacta cgacatgctt atgggtttgt cgagtgcgca | 1100 |
| gtcgttgtcg tcccgcatga tcgggctcaa gtacactgat cctagtgtac | 1150 |
| tcgcgacggt tgcccaatac tatcagggca agaatgttga agttgccgac | 1200 |
| gctgacagga tcggccgcgc cataaatccc aaggtccact ggccagcgca | 1250 |
| cgtcgaagtt gacgaggcgg aggttagtgc tcgggtgtac gccagcccgt | 1300 |
| tggtatctga cgaaaatatg atgcctatga tcaagcgctg ggagacgctg | 1350 |
| tcgttgtcgc tggaccgccg ggttacattc caacgtaatc cgaaggttcc | 1400 |
| tggaaaacgg ctcagggctt atgccattga gttcgttgac ttggttgtgc | 1450 |
| ctgagcgtgg tgtcggagtc ccctattcat tggaggacac cgccgccatg | 1500 |
| ctggacaaac caagccagac cctcgccatc caacaggtgt gggagactgt | 1550 |
| cgacatgccc ccaagaaggc tcatcgaagc gttcgtgaag aacgaaccga | 1600 |
| ccatgaaggc tggccgtatc atctcgtcgt tcgctgacat gcggttccta | 1650 |
| ctgcggtttt ccagctatac gctggcattc cgtgatcagg tgctgcatgc | 1700 |
| agagcacaac cggcattggt tttgcccggg tttgaccccc gagcagatcg | 1750 |
| ccacaaaagt ggttgattac gtgtccggtg ttgaagaacc atcggaggga | 1800 |
| gacttttcca actttgatgg cacggttagt gagtggctac aacgccacgt | 1850 |
| catgaacgcc gtctacctgc gttatttcaa tcaccgagcg cagcgagacc | 1900 |
| tcaggtcgta taccgacatg ctggtctcat gccccgcgag ggcgaagcga | 1950 |
| ttcggttttg cttatgacgc gggtgtcggc gttaagagcg ggtcgccaac | 2000 |
| aacttgcgac ctgaataccg tgtgcaatgg tttcctccaa tattgctcca | 2050 |
| ttcgaatgac acacccagag ctgacaccaa tcgatgcttt ccggctcatc | 2100 |
| ggtctcgcgt ttggggacga ttccctcttc gagcgacgtt tcgctaagaa | 2150 |
| ctatgcgaag gtttccgccg aggtggggat ggtcctcaaa atcgagcgat | 2200 |
| tcgacccggc acaaggcatc actttcctcg cccgtgttta tcccgacccc | 2250 |
| tacacgtcga ccacaagttt ccaggaccct tgcgtacct ggaggaagct | 2300 |
| ccacttgacg acgcgcgatc caacaatacc attggcaacg gctgccatcg | 2350 |
| atcgcgttga gggctacctc gtcaccgacg gcctgagccc gcttactggc | 2400 |
| gcgtattgtc gcatggttaa gcgggtttac gaggccggcg gagccgagga | 2450 |
| tgccgccaag aggaggtcgc gaaaatccca ttcccgcgaa aagccgtatt | 2500 |
| ggttgactgt tggaggcgct tggccccaag atgtcaagga cgttgatctt | 2550 |
| atgttccagt gtgcggccgc acgtaccgga gtagacctcg agacacttcg | 2600 |

-continued

```
gtctctggat cagcgtctag gagaaatcac tgacgtctgg gcggatatta        2650
ccatcaaccg ggataatgaa ccaaacccct acaaggatac actggacttg        2700
gagggcccgg ctgatggccg ggtggacgat cgtgtatttc agaatgacaa        2750
acatgtcatg cgcttacgag ctaatcaagt cacttccagc caagctggag        2800
cagctggctc aggagacgca agcaacgatc caaacgctca tgatcgcgga        2850
tcccaacgtc aacaaggatc tgcgagcgtt ctgcgagttc ctgaccgtgc        2900
agcaccagcg ggcgtatcga gcgacgaaca gcctgctcat caaaccgcga        2950
gtcgcagcag cgcttcgcgg ggaggagctg gacctgggcg aggcggacgt        3000
cgccgcccgg gtccgccagc taaaacaaca gctggcggag ctcgagatgg        3050
aaatcaagcc agggcaccaa caagtggccc aagtaagcgg caggcggaag        3100
gccgcagccg cagctcccgt ggcccagctg ggtcgcgtgg gcgtggtaaa        3150
tgagtgattc atcgtcccat ctgacgaaac ccgaactagg cttatgccag        3200
tggt                                                          3204

<210> SEQ ID NO 2
<211> LENGTH: 1336
<212> TYPE: DNA
<213> ORGANISM: Nodamura virus
<220> FEATURE:
<221> NAME/KEY: gene
<223> OTHER INFORMATION: cDNA of RNA2 genome segment

<400> SEQUENCE: 2
gtaaacaacc aataacatca tggtatccaa agcagcacgc cgccgaagag          50
cggcccctcg acaacaacaa cgacaacagt cgaaccgtgc atcaaaccag         100
cctcgtcgga ggagagctcg ccgtactcga agacagcaga gaatggcagc         150
aacaaacaac atgctgaaaa tgagcgctcc cggactcgat tttctgaaat         200
gtgcctttgc ttcgccggat ttttccaccg atcccggcaa aggtattcca         250
gacaaatttc agggtctcgt tttaccgaag aaacattgtc tgacccagtc         300
gataacgttt actccgggga aacagacgat gctgttggtt gcacctattc         350
ctggaattgc ttgcctgaag gcagaagcga atgttggcgc atccttttca         400
ggtgttcctc ttgcctcagt tgaatttcca gggttcgacc agctgtttgg         450
cacgtcagca actgacaccg cagctaatgt cactgctttc cggtatgcgt         500
caatggcagc cggtgtttac ccccacgagca atctaatgca atttgctggg        550
tcaatacagg tgtacaagat acctctaaaa caggttctta actcctactc         600
tcagaccgta gcgaccgtac cacctaccaa cttggctcag aacacaattg         650
caatagatgg actagaagcg ttagatgcac taccaaataa caactactcc         700
ggttctttta tcgagggttg ttattcacaa tcggtgtgca atgaacctga         750
gtttgagttc catcccatca tggagggtta cgcgtccgtt ccacccgcga         800
acgtaaccaa tgctcaagct agcatgttca ccaatctaac cttctcaggc         850
gcagcatata ccggtcttgg cgacatggac gcaattgcga tccttgtgac         900
tacgcccacc ggtgccgtca acacggccgt gctgaaggtc tgggcctgcg         950
tagagtatcg tccgaatcca aattccaccc tctatgagtt cgctcgtgag        1000
tcaccagcaa acgacgaata cgcgctcgcc gcctatagga aaattgccag        1050
```

```
agatattccg attgccgtcg cttgcaaaga caacgccaca ttttgggaac         1100
gcgtccgatc catcctgaaa tctgggctca actttgcttc gaccatacct         1150
ggccccgtag gagtggcagc gacagggatc aaaggcatca ttgaagccat         1200
tggttccttg tgggtttgat tccacccaca gaagcgttga cgacgcaaaa         1250
cgtccttaaa gcgttgacga cgcaaaacgt ccccaagctc gtagcaccga         1300 ccctatacccc atctctaggg tcttcaacct cttggt                       1336
```

<210> SEQ ID NO 3
<211> LENGTH: 3011
<212> TYPE: DNA
<213> ORGANISM: Pariacoto virus
<220> FEATURE:
<221> NAME/KEY: gene
<223> OTHER INFORMATION: cDNA of RNA1 genome segment

<400> SEQUENCE: 3

```
atgttgtagt acgaaagtac caatggagga gcacataccg ctaccaagtc          50
agtatgagag ccctaaggct tgccgcctta gggtgccgag ctcgcgatgg         100
cttaggtcgt tgcgcccacg gctagccaac tcttgtctcg cgctaaagat         150
ccgtgcgcac gagagtttgg tgaagatacg cttgtgtaag ccatatgatg         200
cccagtcccg gtcgaaaatt atagagaaag tgatcgaacg cagggaaacg         250
aggaaaacgt tggcacatca attaaaggat ttaaaattag taccagtagc         300
acgagaccac actcacggac gtgcggcgaa gtttcgtact tcggcgaaca         350
tctggatgaa tgaggccatg cgagctgctg gatacgagcc ttataatgtg         400
tcaatgagca accacgacat agagagagga accggtatt tttacttcgc          450 aaaggatctc accatacccct acaggaatga tccggtgtcg ataatacag          500 gtttcgtctt ttgtgacgtg gattactatg cagatatgga aaaatggatg         550
cagcacttta aaccaatgtt gttgtataca ttagtaccag aatcgctctc         600
gtatcactgc gatgaccact ccttccacgt gaatgatgat agggttttct         650
ttgacgtgcg aggcggcgcc agctatagtc atcagctatg ggattacact         700
ggcgacacta tctgtgtgag ggggaagaac aaggaactct tggtcttcac         750
catcgaacag aagtgtatcc agggtgaccc acatcgccga ataattttcc         800
ttgaaccagc agccagagtt gcttggccct tttataaacc gatgaaagtt         850
gaggtagggc tgaagcgcaa atgtatgact gcaggtcaag tcaacgtgtt         900
gtatgagcca atagatgata aaatatcttt gtcagctagt ggctcacgcc         950
acactgtaga gaccacggga cggacgctgg cagcaataac tgcacgaatg        1000
aagaataaga cgtcaccacc tatggtcgcc gatgtagagc cattttgcg         1050 tgatgcaggt gacaaggagg cgtgtgtaaa cgcgccaata ctctttgagt        1100
tgataccaga ggcaaaattc cgggtgaatg tagtcaagac gactgccaca        1150 ccaaccccact ttcaaccct tggaccgttg aggaccgagg atggtgagac        1200
ttgtgggcat gctgtgacaa cgaccttggc aacagcccccg gcccttttgc        1250 cgatgagggg tgttaattca gatgtggcga ctgtgaatgg ccgggtgaag        1300
aagccggcaa acacggtcat cccattcaag gagtataagg aatacgcatc        1350
tgaattcgtg gagtttttgg tgccagaacc aggcgtcggc catccatggg        1400
```

| | |
|---|---|
| atacggcagc agtgcgtgaa gtgcaggaca accgccaaca gaaagcacgc | 1450 |
| atcaatatgg tagccgccac cgtttctact cactcatcca accggttaaa | 1500 |
| ggccttttata aaggctgaag catacgccgc gacgaacgat ccgcgtaaca | 1550 |
| tcaccactat ggcacctgag cttacactca tgatgtcatg tttcacgtat | 1600 |
| gcattcaagg agaagatctt gtacgagcag ccgtggtacg gcccaggtaa | 1650 |
| gaccccaaag caagtaggac gcaggcttca gagtatcgcc aaacacggta | 1700 |
| cactggagag tgactactca cgctttgatg gctcaatcag cgaatggctc | 1750 |
| cagaaaaacg tggtcaaagc cgcatacatg cggttcttca agagcacca | 1800 |
| acgaacggag ttccagagct ggtttagcaa agtcttcatg cagatgggca | 1850 |
| ccacgactgc tggtgtgagg tacgaagccg gttggggcac caggagtggt | 1900 |
| agcccgataa ctactgatgg caacactatg ctcaatgcgt tgtggtata | 1950 |
| ctgttgctac cggaagttgt gccacactcc cgccgaggct tggaggaagc | 2000 |
| tcagccaagg tgccctcctg actggcgatg atgctgttct tgcccatgaa | 2050 |
| aatgggttgg aaccggcgtt gctggacgta gtcaagaacc tgggccttaa | 2100 |
| agtcgaagcc aaagtgaatg gtcctgatga ccctgtatcc ttttgcggac | 2150 |
| gtatttatcc acgtcttagt gattgcataa cgagttttca ggatcctttg | 2200 |
| cgtacaattc cgaagttaca cctcacaacc aataaggtg tatctccgga | 2250 |
| acaagcagcg gctaataggg cccacgggta cttggcgacg acaaggcga | 2300 |
| ctccgatcat cggcacttgg gccagacgtg tgatagaact gacgggtgac | 2350 |
| ctcaaggtga aggggccac ccgcgaggag cagtacaagt tgtcaaatgc | 2400 |
| tcaccaacaa cttgatccat cgttaatcga aactgctatg gctaacattc | 2450 |
| taggaataga tgtgggagag ctcaaggctt tggataaagc tgtcagtgaa | 2500 |
| gctaaggccc tggaccagat gccggtcgtc ctcggcaact gctacaaaca | 2550 |
| taagattgaa gcagtagtcg gtggcgaggt agtcggacct gggcctcgtg | 2600 |
| ttgagacagt ggaacctaac catgagcaat cgagcggaac tcctgaagtc | 2650 |
| gtaccagaaa tggcaggaca cagcgagcga cgcgataaat cgtctaatcc | 2700 |
| tagaccaggt ggaaaagcgg aaggcttatc gtcgaaagct ggaaaacctc | 2750 |
| gggtgccacc tcgacccgct gcagaccgaa aggctgcggc aggcagtggc | 2800 |
| aaccgtcgtg gacctactaa cggccgacga cccatccgtg atcgagcacc | 2850 |
| cagaggagga ggaaggccta accctggcac aaccccacct gtgagtaact | 2900 |
| ctgaaaccac cacgactact gccgtagtcc atgcatccgc gtaagcggtg | 2950 |
| cacgtgagca aggtacaacc cgccgtacca acatcctttg ggtaaatccc | 3000 |
| aacgcacggc c | 3011 |

<210> SEQ ID NO 4
<211> LENGTH: 1311
<212> TYPE: DNA
<213> ORGANISM: Pariacoto virus
<220> FEATURE:
<221> NAME/KEY: gene
<223> OTHER INFORMATION: cDNA of RNA2 genome segment

<400> SEQUENCE: 4

| | |
|---|---|
| atgtacaggt ataacatcaa agatggtatc aagaactaag aatcgaagga | 50 |

| | |
|---|---|
| acaaggcaag gaaggtcgtc agtcgcagta ccgctttagt gcccatggca | 100 |
| ccagcgtcac agcgcactgg tccggccccg agaaagccgc gtaagcggaa | 150 |
| ccaagcgctc gtgcgtaatc cacgtttgac agatgcaggt cttgcttttc | 200 |
| tgaaatgtgc gtttgctgcc cctgatttta gtgtggatcc cggtaagggt | 250 |
| attccggaca atttcatgg tcgcacactc gccattaagg attgcaacac | 300 |
| cacgtcggtg gtgtttacac cgaacaccga cacgtacatc gtagtggccc | 350 |
| ccgttccggg gttcgcgtat ttccgcgcag aggtcgcggt tggagcgcaa | 400 |
| cccacaacgt tcgttggtgt gccctaccct acgtatgcca ctaacttcgg | 450 |
| tgctggtagc caaaacgggc ttcctgctgt taacaactac agtaagttcc | 500 |
| gttatgcgtc aatggcctgt gggctttacc ccacaagcaa tatgatgcag | 550 |
| ttttcgggtt cagttcaagt gtggagagtt gacttgaacc tgagtgaggc | 600 |
| tgtcaacccc gctgttactg cgattacccc tgcgccggga gtctttgcaa | 650 |
| acttcgtcga taaacgtatc aatggcctga gaggcatccg ccccttggcg | 700 |
| ccgcgagata actactctgg taactttatc gacggggctt acacctttgc | 750 |
| ctttgataag tccaccgatt ttgagtggtg cgattttgtt cgctcgttgg | 800 |
| agttctcaga atctaatgtt ctgggagcgg caacggcgat gaaactgcta | 850 |
| gctcccggag gtggtactga taacaacgctc accggtttgg gtaacgtaaa | 900 |
| cacattagtg tataagatat ccactccgac gggcgccgtg aacaccgcga | 950 |
| ttctacggac ttggaattgc atcgagcttc agccttacac tgactcggcg | 1000 |
| ctcttccaat tctcagggt ctctccaccc ttcgaccctc tcgctcttga | 1050 |
| gtgttatcac aacctcaaga tgcggtttcc agttgcagtc tcttcacggg | 1100 |
| agaacagcaa gttctgggaa ggtgtcctca gagtgctgaa tcaaatttca | 1150 |
| ggcacactgt cagtgatacc aggtccagtc gggactatta gtgcaggcgt | 1200 |
| tcatcaacta acaggaatgt acatgtaaag gaccccccgcc gccagacccg | 1250 |
| ccgacaatcg cacgtcgtaa aactgcgcgc tcgaaagctc ataaaagaaa | 1300 |
| caaccatggc c | 1311 |

<210> SEQ ID NO 5
<211> LENGTH: 20
<212> TYPE: DNA
<213> ORGANISM: Artificial sequence
<220> FEATURE:
<223> OTHER INFORMATION: Junction between the CMV promoter and the first nucleotide of Nodamura virus RNA1

<400> SEQUENCE: 5

| tagtgaaccg gtattgaatc | 20 |
|---|---|

<210> SEQ ID NO 6
<211> LENGTH: 32
<212> TYPE: DNA
<213> ORGANISM: Artificial sequence
<220> FEATURE:
<223> OTHER INFORMATION: Junction between the GAL1 promoter and the first nucleotide of Nodamura virus RNA1

<400> SEQUENCE: 6

| taataaaagt actgcagtat tgaatccaaa ac | 32 |

NODAVIRUS-LIKE DNA EXPRESSION VECTOR AND USES THEREFOR

CROSS-REFERENCE TO RELATED APPLICATION

This is a division of Application Ser. No. 09/595,346, filed Jun. 14, 2000, now U.S. Pat. No. 6,514,757.

This non-provisional patent application claims benefit of provisional patent application U.S. Ser. No. 60/139,120, filed Jun. 14, 1999, now abandoned.

FEDERAL FUNDING LEGEND

This invention was produced in part using funds obtained through grant R37 AI 18270 from the National Institute of Health. Consequently, the federal government has certain rights in this invention.

BACKGROUND OF THE INVENTION

1. Field of the Invention

The present invention relates generally to the molecular biology of nodaviruses. More specifically, the present invention relates to a nodavirus-based DNA expression vector, in which nodaviral RNA replicases and nodaviral cis-elements amplify a transcript containing a heterologous gene by RNA replication.

2. Description of the Related Art

The nodaviruses are a family of small icosahedral viruses with bipartite, single-stranded, positive-sense RNA genomes. Several different members of the virus family have been isolated from insects and fish larvae, but none from higher animals. However, despite the limited natural host ranges of the viruses, many nodavirus RNA replicase enzymes retain full activity in insect, mammalian, plant, and even yeast cells, and they are among the simplest and most powerful eukaryotic RNA replication enzymes known. Replication by nodavirus RNA replicase enzymes produces large amounts of capped mRNAs in the cytoplasm; for example, after amplification of nodamura virus (NoV) RNAs in baby hamster kidney (BHK21) cells for 24 hours, positive-sense RNA replication products approximate the abundance of ribosomes (about $10^7$ molecules per cell) and dominate the cell's capacity for protein synthesis.

The molecular biology of the Nodaviridae is summarized schematically in FIG. 1 (1,2). Virus particles contain one molecule each of two single-stranded genome segments, RNA1 and RNA2, both of which are required for viral infectivity. These RNAs have 5' caps but no 3' polyadenylate tails. Instead, their 3' ends are blocked by either a covalent modification or an unusual secondary structure. RNA1, which in the well-characterized flock house virus (FHV), contains 3107 nucleotides (nt), encodes the entire viral contribution to the RNA-dependent RNA polymerase (RNA replicase) which replicates both RNA1 and RNA2 genome segments. RNA1 can therefore replicate independently of RNA2 and constitutes an autonomous RNA replicon (3). Its nucleotide sequence shows an open reading frame (ORF) which predicts a 112 kilodalton (kDa) polypeptide (protein A), corresponding to the catalytic subunit of the RNA replicase. During replication of RNA1, a sub-genomic RNA (RNA3), which represents the 3' 387 nt of RNA1, is produced by partial transcription (4). RNA3 encodes, in overlapping reading frames, two small, non-structural proteins of about 11 kDa each (B1 and B2). The functions of these proteins are unknown, and neither appears to be essential for RNA replication.

Flock house virus (FHV) RNA2 contains 1400 nucleotides and encodes protein β, a 45 kDa precursor of the two viral capsid proteins β (40 kDa) and γ (5 kDa) (5). 180 copies of protein β assemble with T=3 icosahedral symmetry around RNA1 and RNA2, forming provirions that co-sediment with mature virus particles but lack infectivity (6). Particle assembly triggers the self-cleavage of α, which yields the mature capsid proteins β and γ. This cleavage stabilizes the particles and renders them infectious (7,8).

It is clear that the nodaviruses, with genomes of only 4.5 kb, are among the simplest of all animal viruses. Nevertheless, their RNAs can replicate abundantly in a wide variety of intracellular environments from yeast to mammalian cells, implying that the necessary host cell factors are conserved. The fact that some nodaviruses can readily establish persistent infections of cells in culture (1,2) indicates that long-term replication of viral RNA is not necessarily cytotoxic. Furthermore, the segmented structure of the nodaviral genome simplifies experimental manipulation of the replicase gene and shows that the RNA replicase functions naturally in trans, a convenient property for its use in an expression vector.

Most expression vectors use DNA-templated transcription to achieve the intracellular accumulation of RNAs, a process that is linearly dependent upon the copy number of the DNA template. The properties of nodaviruses and their RNA replicases create an attractive opportunity for the development of a new type of expression vector. It is the goal of the present invention to provide DNA plasmids which are initially transcribed by a host-cell RNA polymerase to produce primary transcripts from which the RNA replicase is translated. These primary transcripts are then amplified by autonomous, cytoplasmic, RNA replication. The performance of these vectors depends less on the efficiency of primary transcription than on the exponential amplification of the primary transcripts by nodaviral RNA replication. As described above, this process occurs abundantly in a very broad range of host cells and is largely independent of the level of cellular metabolic activity. These plasmid vectors should therefore be suitable for use in insect, mammal, plant and yeast cells, and they may also offer advantages in quiescent cells in which conventional expression vectors oftentimes fail.

The prior art is deficient in the availability of nodavirus-based expression vectors that are amplified autonomously in a cell by RNA replication. The present invention fulfills this long-standing need and desire in the art.

SUMMARY OF THE INVENTION

It is a goal of the present invention to provide a nodavirus-based DNA expression vector that is capable of yielding high levels of recombinant transcripts and/or proteins in a wide spectrum of cell types. The vector contains a promoter site for aDNA-dependent RNA polymerase to drive the synthesis of a primary transcript. The primary transcript minimally contains two sequence elements. At the 5' end, the primary RNA transcript contains an open reading frame for a catalytic subunit of an RNA-dependent RNA polymerase (RNA replicase) from a nodavirus, preferably flock house virus (FHV), Nodamura virus (NoV) or Pariacoto virus (PaV). Translation of the 5' open reading frame of the chimeric primary transcript in cells transfected with the nodavirus-based DNA expression vector using host-cell machinery produces an active nodavirus RNA-dependent RNA polymerase, which subsequently recognizes and replicates the primary transcript. Additionally included in the primary RNA transcript are the nodaviral cis-acting signals required for recognition by the RNA replicase. The cis-acting signals flank, at least, the heterologous gene that encodes a desirable transcript and/or protein (e.g., a ribozyme, an antisense RNA, or a protein with therapeutic potential) such that the transcript encoded by the heterologous gene is amplified by RNA replication. Preferably, cis-elements are positioned such that the transcript encoding the RNA replicase is also replicated and subsequently amplified. This strategy produces abundant levels of capped, functional mRNAs in the cytoplasm which are readily expressed by the host cell. Attractive features of this novel type of expression vector are its high expression levels and broad host range.

One object of the present invention is to provide a nodavirus-based DNA expression vector.

In an embodiment of the present invention, there is provided an isolated cDNA encoding a Nodamura virus (NoV) RNA1 genome segment having the sequence shown in SEQ ID No. 1; an isolated cDNA encoding a Nodamura virus (NoV) RNA2 genome segment having the sequence shown in SEQ ID No. 2; an isolated cDNA encoding a Pariacoto virus (PaV) RNA1 genome segment having the sequence shown in SEQ ID No. 3; and an isolated cDNA encoding a Pariacoto virus (PaV) RNA2 genome segment having the sequence shown in SEQ ID No. 4.

In another embodiment of the present invention, there is provided a nodavirus-based DNA expression vector comprising: a DNA-dependent RNA polymerase promoter; a cDNA encoding a nodaviral RNA-dependent RNA polymerase (RNA replicase) which is operably linked to the RNA polymerase promoter; a heterologous gene; nodaviral cis-elements which flank the RNA replicase cDNA and the heterologous gene; and a cDNA encoding a ribozyme that cleaves the transcripts of the expression vector, wherein said cleavage generates 3' ends recognized by the RNA replicase for RNA replication of the transcripts.

In yet another embodiment of the present invention, there is provided a method of replicative amplification of a transcript encoded by a nodavirus-based DNA expression vector in a cell, comprising the step of introducing into the cell the expression vector or a RNA transcript of the vector disclosed herein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 5A shows mortality of the insects monitored at 16 days post-injection. FIG. 5B shows weights of the larvae both at the time of injection and 16 days post-injection. The higher level of mortality and lower weights observed in the test insects indicates that infectious virus was produced in the BsrT7 cells transfected with PaV cDNA clones.

DETAILED DESCRIPTION OF THE INVENTION

Figure 1:
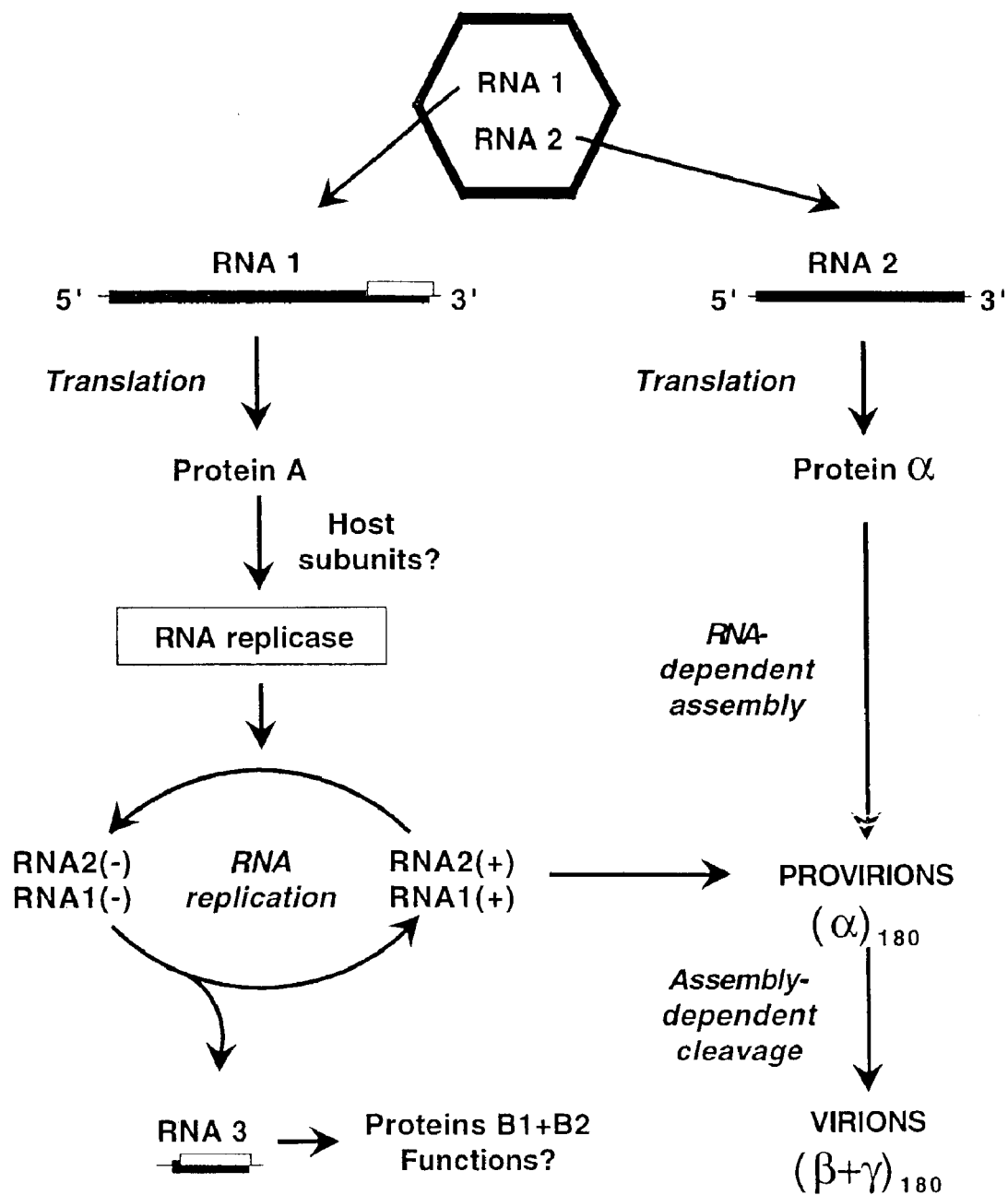
FIG. 1 shows the molecular biology of the Nodavirus genome.

One aim of the present invention is to provide a nodavirus-based DNA expression vector capable of yielding high levels of a heterologous transcript and/or protein in a wide spectrum of cell types. The vector contains a promoter site for a host cell's DNA-dependent RNA polymerase positioned to drive the synthesis of a primary transcript. The primary transcript contains at least two sequence elements. At the 5' end, the primary RNA transcript contains an open reading frame for a catalytic subunit of a nodaviral RNA-dependent RNA polymerase (RNA replicase). Translation of this chimeric transcript in transfected cells by the host cell translational machinery produces active nodavirus RNA replicase, an enzyme which can replicate mRNAs carrying appropriate cis-acting signals in mammalian, avian, insect, plant, and yeast cells. Therefore, cis-acting signals recognized by the replicase and required for replication flank the RNA replicase gene and a heterologous gene that encodes a desirable transcript and/or protein (e.g., one with therapeutic potential).

When flanked by appropriate cis-acting signals, heterologous RNA sequences are replicated efficiently by nodavirus replicases, thereby producing abundant levels of capped and functional mRNAs directly in the cytoplasm. Therefore, this powerful RNA amplification system provides a valuable eukaryotic expression vector. Since DNA is easier and cheaper to prepare, store, and deliver to cells than RNA, the invention herein utilizes DNA plasmid vectors which, when introduced into cells and transcribed into RNA, launch cytoplasmic RNA replication and therefore, amplification of the transcript and/or protein encoded by the heterologous gene contained on the DNA vector.

The present invention is directed towards a nodavirus-based DNA expression vector.

The present invention is directed towards an isolated cDNA encoding a Nodamura virus (NoV) RNA1 genome segment having the sequence shown in SEQ ID No. 1; an isolated cDNA encoding a Nodamura virus (NoV) RNA2 genome segment having the sequence shown in SEQ ID No. 2; an isolated cDNA encoding a Pariacoto virus (PaV) RNA1 genome segment having the sequence shown in SEQ ID No. 3; and an isolated cDNA encoding a Pariacoto virus (PaV) RNA2 genome segment having the sequence shown in SEQ ID No. 4. The present invention is also directed towards DNA vectors comprising the Nodamura virus and Pariacoto virus cDNAs of the present invention, and host cells transfected with those DNA vectors.

The present invention is further directed towards a nodavirus-based DNA expression vector comprising: a DNA-dependent RNA polymerase promoter; a cDNA encoding a nodaviral RNA-dependent RNA polymerase (RNA replicase) which is operably linked to the RNA polymerase promoter; a heterologous gene; nodaviral cis-elements which flank the RNA replicase cDNA and the heterologous gene; and a cDNA encoding a ribozyme that cleaves the transcripts of the expression vector, wherein said cleavage generates 3' ends recognized by the RNA replicase for RNA replication of the transcripts.

The present invention is also directed towards a method of replicative amplification of a transcript encoded by a nodavirus-based DNA expression vector in a cell, comprising the step of introducing into a cell a nodavirus-based DNA expression vector of the present invention or a RNA transcript encoded by the expression vector.

Preferably, the expression vector comprises nodaviral genome segment RNA1, and cis-acting signals for RNA replication or transcription derived from RNA1, RNA2, or RNA3. The expression vector may further comprise a sequence that signals transcriptional termination by the bacteriophage T7 RNA polymerase; or eukaryotic poly(A) and/or transcriptional termination signals, wherein the poly (A) and/or the transcriptional termination signals are 3' of the cis-elements.

Representative RNA polymerase promoters are inducible promoters, constitutive promoters, tissue-specific promoters, and synthetic promoters. Representative inducible promoters are the hormone-responsive Hsp70 promoter, a metallothionein promoter, an alcohol dehydrogenase promoter and a galactose promoter; representative constitutive promoters are the Rous sarcoma virus (RSV) LTR promoter, the human cytomegalovirus (CMV) major immediate early gene promoter and the SV40 early promoter; and representative tissue-specific promoters are an alpha globin promoter and a beta globin promoter.

Typically, the nodaviral RNA replicase and the nodaviral cis-elements are from a nodavirus such as flock house virus, Nodamura virus and Pariacoto virus. Representative means of introducing the nodavirus-based DNA expression vector include, but are not limited to, injection (including via the 'gene gun'), transfection (with or without lipid or other carrier), or infection by an organism with a DNA genome into which the appropriate vector sequences have been inserted (e.g., a member of the following virus families: adenovirus, herpesvirus, parvovirus, baculovirus, papovavirus, etc.). In general, the heterologous gene may be a gene encoding a desirable transcript and/or protein such as a ribozyme, an antisense RNA, a protein with therapeutic potential, or a gene encoding the cystic fibrosis transmembrane conductance regulator, a gene encoding the herpes simplex virus thymidine kinase, a gene encoding polynucleotide phosphorylase, a gene encoding alpha-globin or a gene encoding beta-globin.

It will be apparent to one skilled in the art that various substitutions and modifications may be made to the invention disclosed herein without departing from the scope and spirit of the invention.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotide bases (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. The DNA and/or RNA structures are discussed herein according to the normal convention of giving only the sequence in the 5' to 3' direction along the nontranscribed strand of DNA or RNA (i.e., the strand having a sequence homologous to the mRNA).

A "vector" is a DNA replicon, such as a plasmid, cosmid, bacteriophage, or virus, to which another DNA segment may be attached so as to bring about the replication of the attached segment. A "replicon" is any genetic element (e.g., plasmid, chromosome, or component of a viral genome) that functions as an autonomous unit of DNA or RNA replication in vivo; i.e., capable on its own of replication in an appropriate intracellular environment. As used herein, 'autonomous' means containing, typically in a single covalently-joined molecule, all the genetic information and cis-acting regulatory sequences necessary to bring about its own replication when the molecule is introduced into a suitable intracellular environment. An "origin of replication" refers to those DNA or RNA sequences that direct and regulate the initiation of DNA or RNA synthesis. An "expression control sequence" is a DNA or RNA sequence that controls and regulates the transcription and/or translation of another DNA or RNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with a particular host cell. The expression vector typically contains an origin of replication, promoter(s), terminator(s), as well as specific genes which are capable of providing phenotypic selection for host cells carrying the expression vector. Additionally, an expression vector may be introduced into more than one host cell, which requires appropriate promoter sequences and/or origins of replication for each host, such that the desired gene(s) are expressed, or the vector replicated, in the appropriate host cell(s). Transformed cells can be fermented and cultured according to means known in the art to achieve optimal cell growth. Generally, *E. coli* is a host cell used to prepare and obtain sufficient amounts of a vector, such as a plasmid. These types of 'host cells' may be distinct from such 'host cells' in which the vector is used (e.g., mammalian cells, human tissue, etc.).

A DNA "coding sequence" is a double-stranded DNA sequence which is transcribed into RNA and the RNA translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, sequences from the genomes of viruses that infect prokaryotes or eukaryotes, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from a mRNA transcript. An "exon" is a sequence transcribed from the gene locus that is expressed as protein, whereas an "intron" is a non-expressed sequence from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence that interacts with protein(s) which can upregulate or downregulate expression of a specific gene locus. As used herein, "nodaviral cis-elements" are nucleotide sequences that are recognized by the nodaviral RNA replicase and direct replication of the transcript. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction on the non-transcribed strand) coding sequence. For purposes of defining the present invention, the promoter sequence is bounded at its 3' terminus by the transcription initiation site and extends upstream (5' direction on the non-transcribed strand) to include the minimum number of nucleotides necessary to initiate transcription at levels detectable above background. Additionally, promoter sequences may extend upstream (5' direction on the non-transcribed strand) to include all nucleotides that affect, qualitatively or quantitatively, the operation and/or efficiency of the promoter. Within the promoter sequence will be found a transcription initiation site, as well as protein binding domains responsible for the binding of RNA polymerase. Eukaryotic promoters often, but not always, contain "TATA" boxes and "CAT" boxes. Prokaryotic promoters contain −10 and −35 consensus sequences in addition to the Shine-Delgarno ribosome-binding sequences that direct translation.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary or other cell that is capable of stable growth in vitro for many generations. An organism, such as a plant or animal, that has been transformed with exogenous DNA is termed "transgenic".

As used herein, the term "host" is meant to include not only prokaryotes, but also eukaryotes, such as yeast, plant and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Saccharomyces cerevisiae, Pichia pastoris*, mammalian cells, insect cells, and plant cells, such as *Arabidopsis thaliana* and *Tobaccum nicotiana*.

A "heterologous" region or gene of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence itself may not be found in nature (e.g., a cDNA, in which the genomic coding sequence contains introns, or synthetic sequences having codons different from the native gene). Allelic variations or naturally-occurring mutational events do not give rise to a heterologous region of DNA as defined herein.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of the gene in transgenic systems, in accordance with conventional Southern hybridization techniques known to those of ordinary skill in the art. Both the Northern blot and Southern blot use a hybridization probe, e.g., radiolabelled cDNA or RNA, either containing the full-length, single stranded DNA or RNA or a fragment of the sequence at least 20 (preferably at least 30, more preferably at least 50, and most preferably at least 100 consecutive nucleotides in length). The DNA hybridization probe can be labelled by any of the many different methods known to those skilled in this art.

As used herein, the term "nodavirus-based DNA expression vector" refers to one or more DNA expression vectors that rely upon the expression of a nodaviral RNA-dependent RNA polymerase to replicate and thereby amplify a transcript produced from the DNA expression vector.

As used herein, the term "replicative amplification" refers to an increase in the number of transcripts due to RNA replication. In the present invention, replication is of a primary RNA transcript resulting originally from transcription of a DNA vector, or nucleotide sequence contained therein.

It is contemplated that pharmaceutical compositions may be prepared using the novel nodavirus-based DNA expression vector of the present invention. In such a case, the pharmaceutical composition comprises the novel nodavirus-based DNA expression vector of the present invention and a pharmaceutically acceptable carrier. A person having ordinary skill in this art would readily be able to determine, without undue experimentation, the appropriate dosages and routes of administration of the nodavirus-based DNA expression vector of the present invention. The dose, dosage regimen and routes of administration will depend upon the nature of the particular disease, the characteristics of the particular nodavirus-based DNA expression vector, e.g., its therapeutic index, the patient, the patient's history and other factors. The schedule will be continued to optimize effectiveness while balanced against negative effects of treatment. See Remington's Pharmaceutical Science, 17th Ed. (1990) Mark Publishing Co., Easton, Penn.; and *Goodman and Gilman's: The Pharmacological Basis of Therapeutics* 8th Ed (1990) Pergamon Press. When used in vivo for therapy, the nodavirus-based DNA expression vector of the present invention is administered to the patient or an animal in therapeutically effective amounts (e.g., amounts that eliminate or reduce a tumor burden). For administration, the nodavirus-based DNA expression vector will most typically be formulated in association with a pharmaceutically acceptable vehicle. Such vehicles are preferably non-toxic and non-therapeutic. Examples of such vehicles are water, saline, Ringer's solution, dextrose solution, and 5% human serum albumin. Non-aqueous vehicles such as fixed oils and ethyl oleate may also be used. Liposomes may be used as carriers. The vehicle may contain minor amounts of additives such as substances that enhance isotonicity and chemical stability, e.g., buffers and preservatives.

The following examples are given for the purpose of illustrating various embodiments of the invention and are not meant to limit the present invention in any fashion:

EXAMPLE 1
Expression and Replication of Nodavirus cDNAs

Full-length functional cDNA clones of the two genomic segments of flock house virus can be transcribed into infectious RNAs by phage RNA polymerases in vitro (11) or in vivo (10,12–14), or by Vaccinia virus (VV) RNA polymerase in vivo (15). Using this approach to study flock house virus RNA replication, it was found that terminal extensions at either end of the cDNA-templated primary transcripts severely inhibited their subsequent replication (10,12–14) (Table 1). 5' extensions were avoided by precise positioning of the DNA-dependent RNA polymerase promoter, and the cis-acting ribozyme from hepatitis delta virus (HDV) was used to generate perfect 3' ends by self-cleavage of the primary transcripts (10,14,16). This approach allowed reconstruction of flock house virus RNA replication from DNA plasmids with an efficiency that approached that of the native virus.

TABLE 1

| Terminal extensions | | Replication |
|---|---|---|
| 5' | 3' | % |
| (Authentic RNA1) | | (100) |
| 26 | 43 | 0 |
| 26 | 12 | <1.0 |
| 10 | 12 | 1.0 |
| 2 | 12 | 11.3 |
| 1 | 12 | 54.1 |
| 1 | 0 | 96.9 |

EXAMPLE 2
Primary Transcription by RNA Polymerase II

The previous experiments used *Vaccinia* virus (VV) promoters to drive synthesis of the primary nodaviral transcript in the cytoplasm of *Vaccinia* infected cells, and were thus limited to cells that could be infected by *Vaccinia* and by the duration of the *Vaccinia* replication cycle. To circumvent these limitations and achieve primary transcription in uninfected cells, the *Vaccinia* promoter was replaced with a promoter for cellular RNA polymerase II (pol II) (either the SV40 early promoter, the Rous sarcoma virus (RSV) LTR promoter (20) or the hormone-responsive Hsp70 promoter (21)). In all constructs, the promoter was positioned to initiate pol II transcription precisely at the 5' end of the flock house virus cDNA, and the HDV ribozyme was positioned to cleave the primary transcript precisely at the 3' end of the flock house virus cDNA-encoded sequences. Furthermore, the expression vector may contain 3' signals for transcriptional termination and/or polyadenylation, such that a primary transcript with defined 5' and 3' ends is produced. The expression vectors constructed herein additionally contain a sequence that signals transcriptional termination by the bacteriophage T7 RNA polymerase. Results determined that this sequence assists the hepatitis delta virus ribozyme mediate its RNA cleavage reaction, even in transcripts that do not terminate at the T7 transcriptional termination site. Transfecting these expression plasmids into BHK21 cells established flock house virus RNA replication in the cytoplasm, and allowed application of the vector in a non-cytocidal situation (20). Co-transfection of plasmids containing cDNAs corresponding to both flock house virus RNA1 and RNA2 re-created the characteristic pattern of RNA replication in FHV-infected cells, i.e., coordinated replication of RNA1 and RNA2 genomic segments and suppression of RNA3 synthesis (3, 20).

EXAMPLE 3

Replication of Dimeric Primary Transcripts

The expression vector system described herein depends upon the expression of two genes: the gene for a nodavirus RNA replicase (i.e., RNA-dependent RNA polymerase) and a heterologous gene that encodes a desired transcript and/or protein. For an optimal expression system, it was therefore necessary to design a convenient and reliable way to deliver the two genes to the same cell in a coordinated manner.

In a series of experiments designed to examine how far the nodaviral RNA structures could be altered without losing their ability to replicate, it was found that both RNA1 and RNA2 replicate efficiently from primary transcripts that contained tandem copies of either RNA1 or RNA2. During replication, the homodimeric transcripts were resolved into their monomeric components, with the 5' and 3' copies replicating with approximately equal efficiency. Therefore, it is feasible to deliver both RNA replicons from a single heterodimeric primary transcript produced from a single promoter. This approach has the advantage of a single plasmid system (containing about 6 kb plus the size of the heterologous gene) which delivers equimolar amounts of the replicase gene and the heterologous gene to transfected cells. Since eukaryotic ribosomes usually translate only the 5'-most open reading frame in an mRNA transcript, the gene encoding the replicase should be positioned 5' of any other genes present on the expression vector, such that the replicase messenger RNA is translated and subsequently amplifies the segment containing the heterologous gene.

EXAMPLE 4

Inducible Transcription by RNA Polymerase II

The next step in the development of this expression system was to bring primary transcription of the cDNA encoding the RNA replicase and the heterologous gene under the control of an inducible pol II promoter. For this, the Hsp70 promoter from *Drosophila* was chosen (21). No et al. previously engineered this promoter to be responsive to ecdysone analogs for use in mammalian cells and transgenic mice (22). Since ecdysone has no apparent effect on mammals, this system provides highly specific control over transgene expression, both in cultured cells and in experimental animals.

A plasmid that contained FHV1 cDNA immediately downstream of the hormone-responsive Hsp70 promoter was transfected into Chinese hamster ovary (CHO) cells expressing a modified ecdysone receptor, and transcription was induced with the corresponding ecdysone analog, muristerone A. A high level of RNA replication was observed by measuring the incorporation of [$^3$H]-uridine into flock house virus RNA1 and RNA3 (21).

FIG. 2 shows the gel profile of cytoplasmic RNAs labeled during 2 hr pulses given daily after hormone treatment of plasmid-transfected CHO cells. Actinomycin D was included during labeling to inhibit incorporation due to DNA-templated transcription. In the continuous presence of the inducing hormone, RNA replication persisted for at least 10 days. However, when the hormone was withdrawn, RNA replication diminished and became undetectable after about 3 days.

EXAMPLE 5

Cells That Stably Express RNA Replicase

A selectable marker gene that encoded G418-resistance was included in the FHV1 plasmid to enable isolation of stable cell lines that express the RNA replicase. After being maintained in culture for more than 6 months, these cells still responded to hormone treatment by inducing RNA replication. Moreover, repeated short exposures (e.g., 7 days apart) to the hormone resulted in repeated induction of RNA replication without any evidence of cytopathology. These results strongly suggest that repeated bursts of RNA replication was not detrimental to the viability of the cells.

EXAMPLE 6

Cis-Acting Signals for RNA2 Replication

The replication of negative-sense RNA2 transcripts (14) was also examined to map the required cis-acting signals (13,17). Three major cis-acting signals were identified in flock house virus RNA2 positive strands: the first three nucleotides at the 5' end, an internal region of about 200 nt between nt 520–720 and 60 nt at the 3' terminus (13,17). The role of the internal element is unclear, but it can be moved relative to either termini of RNA2 without disturbing replication. In the vectors constructed herein, the internal element was placed downstream (3') of the heterologous gene, such that the open reading frame of the heterologous gene is closest to the 5' end of the (resolved) RNA2-derived molecule.

Additional results demonstrated that heterologous sequences (e.g., a therapeutic gene) inserted near the 5' end of RNA2 do not interfere with replication of the chimeric RNA. Furthermore, a naturally-occurring deletion of RNA2 can support the replication and expression of both the chloramphenicol acetyltransferase (CAT) open reading frame (18) and the yeast ura3 open reading frame (19) when either gene is placed near the 5' end of the RNA. Indeed, the CAT open reading frame was inserted at several positions along the length of RNA2 without destroying the ability of the chimeric RNA to replicate. These data suggest that the replication of RNA2 and its derivatives is relatively robust and insensitive to major changes in RNA sequence and structure.

Significantly, the RNA2 sequence from NoV was published by Dasgupta & Sgro in 1989 (27). However, the published sequence ended at nucleotide 1335 with an unknown base (i.e., X). Therefore, the published sequence lacked the last two nucleotides of the 3' end of the RNA2. The 3' nucleotides are reported herein to be critical for replication of the RNA2 genome segment. Accordingly, the NoV RNA2 sequence published be Dasgupta & Sgro would not be able to replicate, as the entire cis-element necessary was not identified.

EXAMPLE 7
Cloning and Sequencing of Nodamura Virus (NoV) and Pariacoto Virus (PaV) RNA1 and RNA2

Although many properties of the FHV RNA replicase make it well-suited for use as the basis of a versatile expression vector, it is temperature-sensitive and loses enzyme activity at normal incubation temperatures for vertebrate cell cultures. However, the RNA replicase from the related Nodamura virus (NoV) and the related Pariacoto virus (PaV) retain activity over a wider temperature range that extends to 37° C. and above (23). Therefore, full-length functional cDNA clones of NoV RNA1 (3.2 kb) (SEQ ID NO. 1) and RNA2 (1.34 kb) (SEQ ID NO. 2) and full-length functional cDNA clones of PaV RNA1 (3.01 kb) (SEQ ID NO. 3) and RNA2 (1.31 kb) (SEQ ID NO. 4) were obtained. Sequence analysis of the RNA1 cDNAs shows: the NoV replicase is approximately 44% identical to the FHV enzyme at the amino acid level; the PaV and FHV cDNAs demonstrate 35% amino acid sequence identity; and the PaV and NoV RNA1 cDNAs possess 27% amino acid sequence identity. Sequence analysis of the RNA2 cDNAs shows: 40% amino acid sequence identity between PaV and FHV cDNAs; the PaV and NoV cDNAs exhibit 39.4% amino acid sequence identity; and FHV and NoV RNA2 cDNAs possess 51.5% amino acid sequence identity.

EXAMPLE 8
Construction of a Nodavirus-Based DNA Expression Vector

Figure 5A:
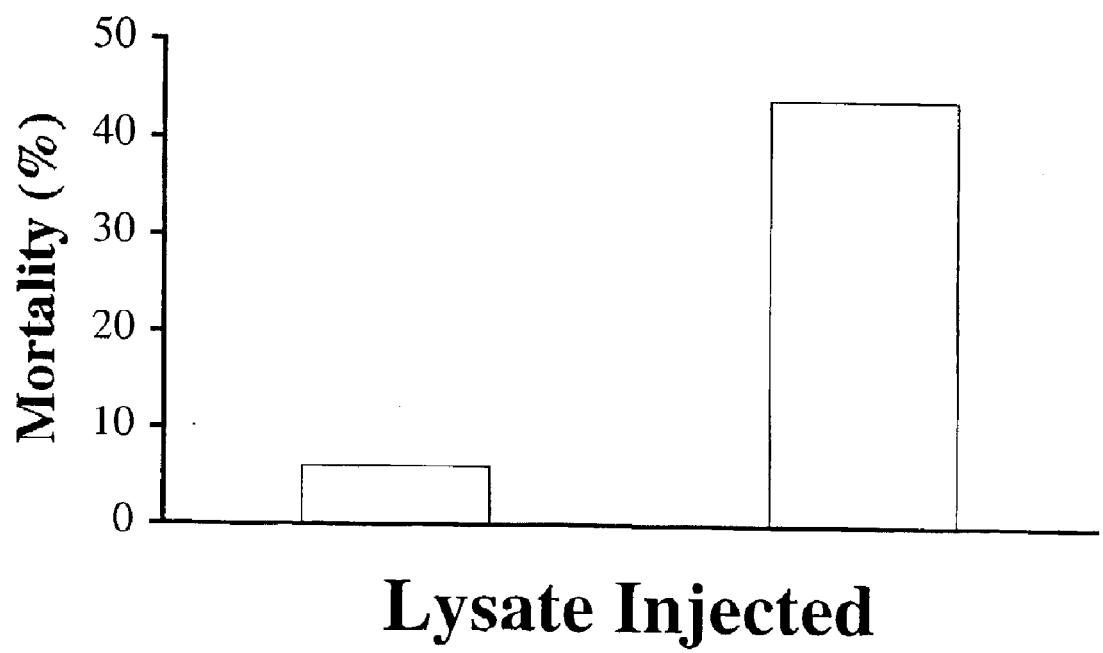
FIGS. 5A and 5B show virus recovered from PaV cDNA clones is infectious for *Galleria mellonella* larvae. BsrT7 cells were transfected with cDNA plasmids of PaV RNA 1 and 2 or mock transfected. Forty-eight hours post-transfection, the cells were lysed and whole cell lysates were injected into groups of 16 insects.
Figure 5B:
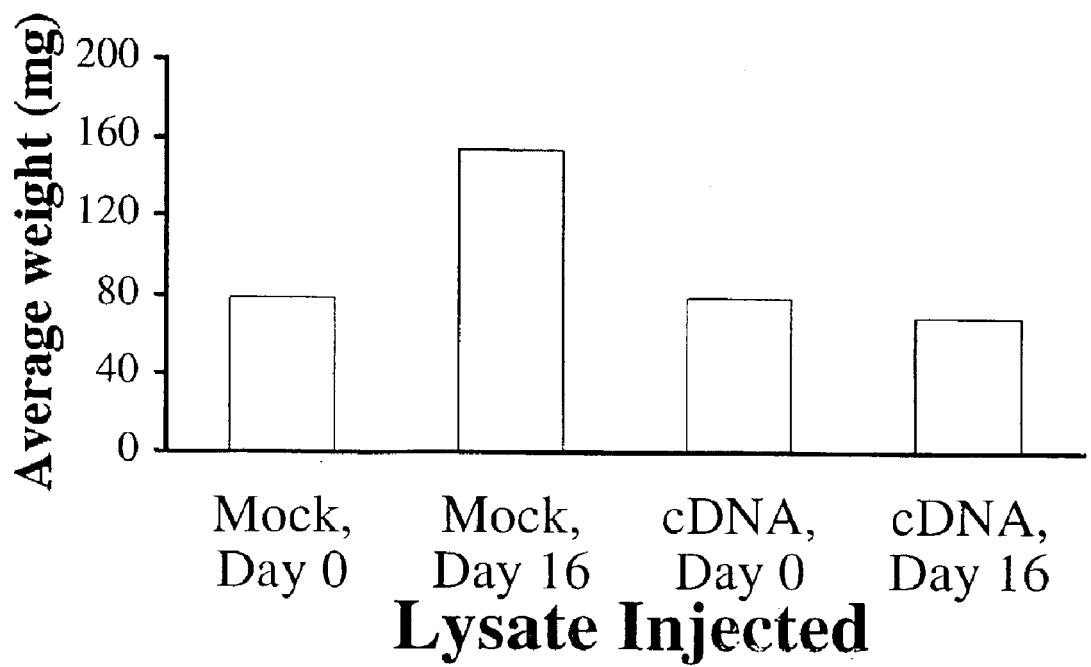

A DNA plasmid was constructed that directs, from a single inducible RNA polymerase II promoter, synthesis of a heterodimeric RNA1-RNA2 primary transcript that contains all the cis-acting signals required for the replication of each individual component (FIG. 5). Previous results with nodaviral RNA replication (10,12–15,20) suggest that optimal replication of the primary transcripts requires that: the promoter initiates transcription precisely at the 5' end of the RNA1 cDNA; the internal junction perfectly juxtaposes the 3' end of RNA1 with the 5' terminus of RNA2; and the site-specific cleavage occurs exactly at the 3' nucleotide of the RNA2 sequence. In the vector disclosed herein, site-specific cleavage is mediated by the hepatitis delta virus (HDV) ribozyme, which cleaves the heterodimeric primary transcript to produce an appropriate 3' end that is recognized by the RNA replicase. The hepatitis delta ribozyme is the most convenient ribozyme for the nodavirus-based DNA expression vectors because this particular ribozyme naturally produces the appropriate 3' end required for replication of the genome segment by the RNA replicase. Numerous other ribozymes are envisioned (e.g., from the 'hammerhead', 'hairpin', or 'pseudoknot' categories of ribozyme structure), but these ribozymes require modifications to produce the desired cleavage.

Figure 2:
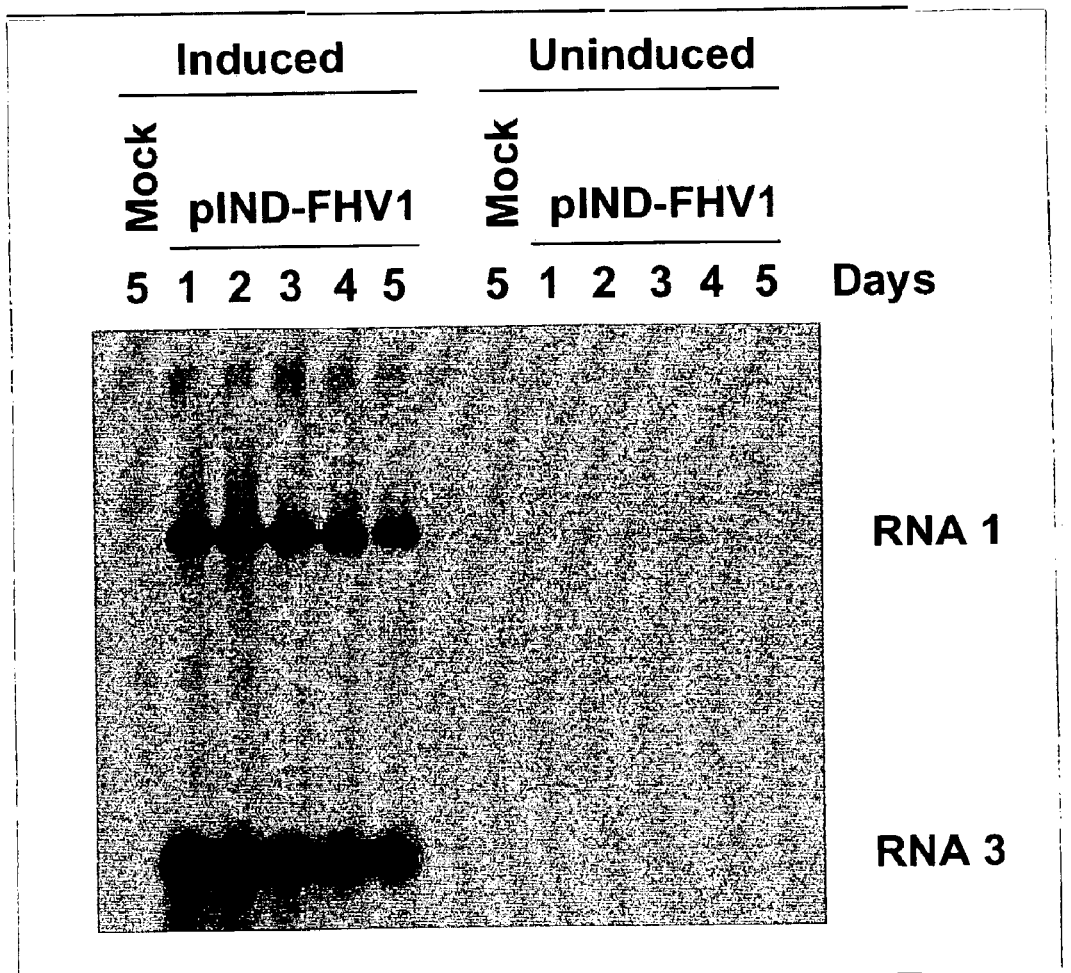
FIG. 2 shows FHV RNA replication initiated by induction of transcription from a hormone-responsive pol II promoter.
Figure 3:
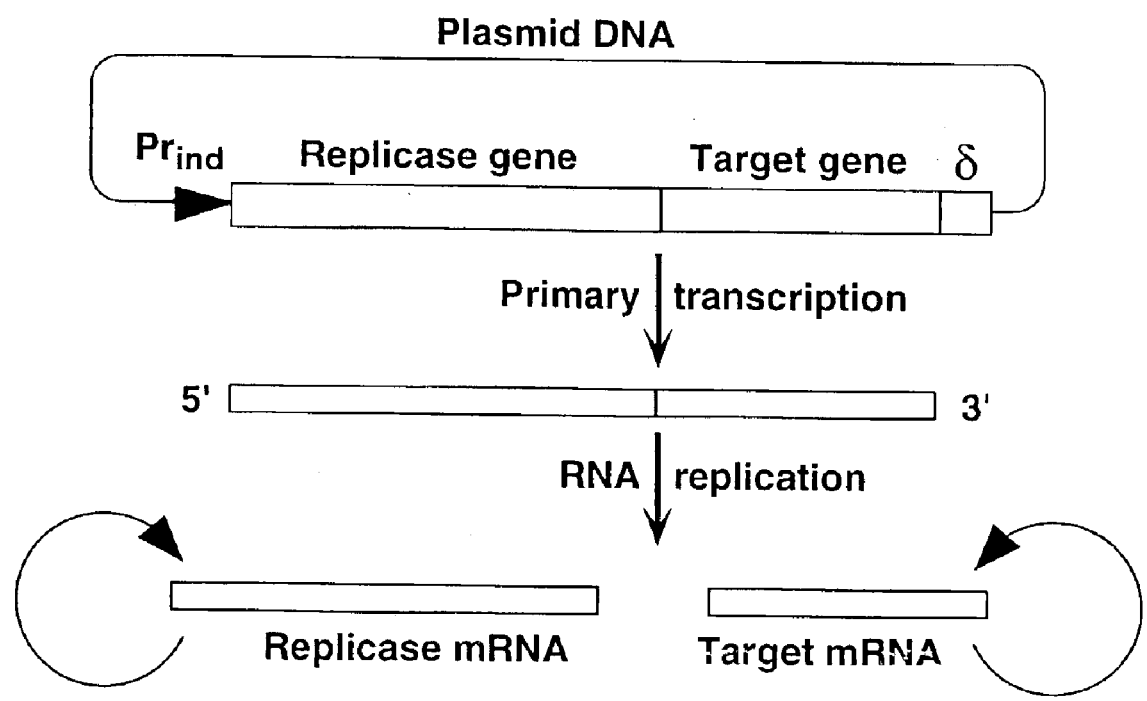
FIG. 3 shows the design and operation of tandem replicon plasmids. Optimal replication of the primary transcripts requires that: i) the promoter ($Pr_{ind}$) initiates transcription precisely at the 5' end of the replicase gene; ii) the internal junction perfectly juxtaposes the 3' end of the replicase gene with the 5' terminus of the target gene; iii) the site-specific cleavage occurs exactly at the 3' nucleotide of the target gene sequence. In the vector disclosed herein, site-specific cleavage is mediated by the hepatitis delta virus (HDV) ribozyme ($\delta$). It is anticipated that such heterodimers may be resolved into their monomeric components, provided that the replicase gene occupies the 5'-proximal position and therefore can be directly translated. Circular arrows indicate replication of the separate components contained within the primary transcript.
Figure 4:
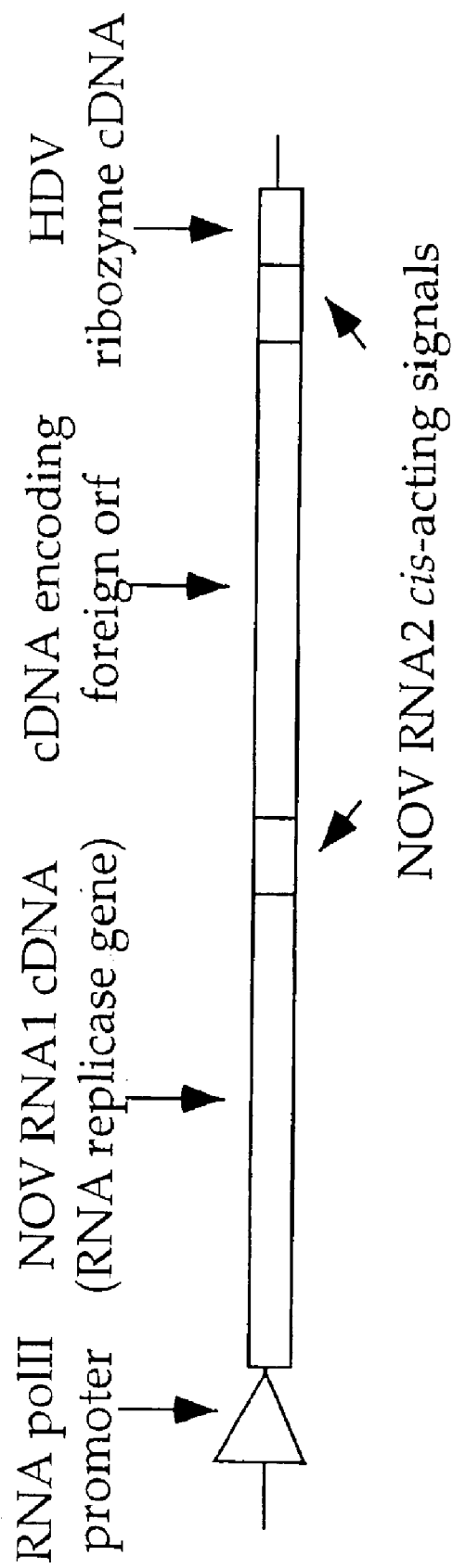
FIG. 4 shows the arrangement of DNA sequence elements in a versatile expression plasmid designed to express high levels of foreign gene products when transfected into many different cell types. Initially transcribed by cellular RNA polymerase II, the foreign mRNAs will be amplified by RNA replication catalyzed by the RNA-dependent RNA polymerase (RNA replicase) of one of the nodaviruses. The sequences necessary for replication and selection in *E. coli* have been omitted for simplicity.

The current pol II-driven replication system described herein uses the inducible promoter system of No et al. (22) and hormone-responsive CHO cells (see FIG. 2). It is recognized, however, that this promoter is not ideal for a general expression plasmid, since it depends upon specialized cells that express the hormone-response element (22). Additional promoters, namely other constitutive and inducible pol II promoters, such as the metallothionein promoter, the human cytomegalovirus major immediate early promoter and the *Drosophila* beta-actin promoter are utilized in the present invention. The ability of the NoV or PaV RNA1-RNA2 plasmids to direct RNA replication in transfected cells is examined, and resolution of the replication products into the correct individual RNA replicons is confirmed. Proper resolution is an essential component of the expression system, because the heterologous gene should not be translated from its position as the 3' cistron in the bicistronic primary transcript.

Plasmids are constructed from full-length, functional cDNA clones of NoV or PaV RNA1 and RNA2 using overlapping polymerase chain reactions (PCR) to create the required flanking and internal junctions (FIG. 5). The authenticity of the junctions and all PCR-generated DNA regions are confirmed by sequencing. The plasmids are transfected into cells using LipofectAmine (20). RNA replication is assayed by metabolic incorporation of [$^3$H]-uridine in the presence of actinomycin D, followed by electrophoresis of the labeled RNAs on denaturing agarose-formaldehyde gels and visualization by fluorography. The effect of several variables on RNA replication is examined, including input plasmid concentration, duration of hormone treatment, and the time and temperature of incubation. Replication products are characterized by comparison with authentic monomeric RNAs 1, 2 and 3, and confirmed by primer extension analysis. Alternately, a plasmid that contains separate DNA-dependent RNA polymerase promoters to transcribe the two cDNAs, or two separate plasmids that contain cDNAs of RNAs 1 and 2, may also be useful in the present invention. In the case of the former, the additional RNA polymerase promoter may or may not be provided by the heterologous gene.

Figure 6:
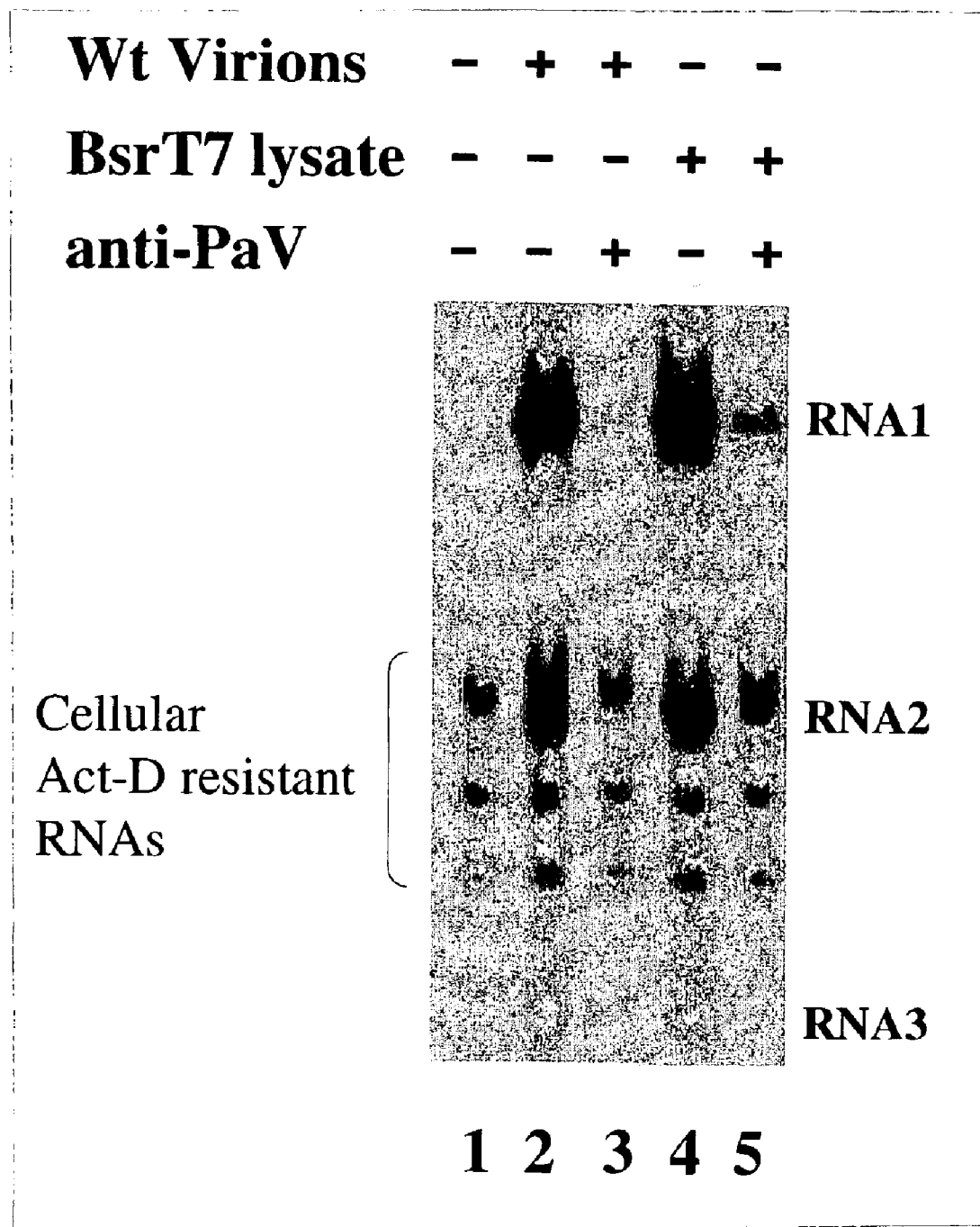
FIG. 6 shows infectivity of authentic and recombinant PaV in fat-body 33 (FB33) cells from the corn earworm, *Helicoverpa zea*. Lanes 2 and 3 shows RNA replication products following infection of *Helicoverpa zea* FB33 cells with purifed wild type PaV virions; lanes 4 and 5 shows lysates recovered from BsrT7 cells transfected with cDNA plasmids of PaV RNAs 1 and 2; lane 1 shows lysates from mock transfected BsrT7 cells. Prior to infection, the samples were either left untreated (lanes 2 and 4) or neutralized with PaV specific polyclonal antibody (lanes 3 and 5). Metabolically labeled RNAs were separated on a denaturing-agarose gel. The positions of RNAs 1 and 2 and subgenomic RNA 3 are shown. Both the virion sample and the cell lysates were neutralized by the PaV specific antisera, indicating production of infectious virions from PaV cDNA clones.

EXAMPLE 9
RNA-dependent RNA Polymerase Replication of the Resultant Transcript from the Expression Vector The next step is to harness RNA replication to drive the amplification of foreign mRNAs. To this end, the tandem delivery plasmid (FIG. 5) is modified by inserting a heterologous gene, in this case for experimental purposes, a reporter gene, as the 5'-proximal open reading frame in the RNA2 sequence (FIG. 6). Genes encoding firefly luciferase, lacZ, G418 resistance or the green fluorescent protein (GFP) are introduced into the downstream RNA2 replicon such that their open reading frames are flanked by the RNA2 cis-acting signals and positioned to initiate translation at the first AUG codon of the chimeric RNA2. To provide a versatile eukaryotic vector for general use, the insertion site for the reporter gene is flanked by several unique restriction sites for convenient cloning of other target genes, i.e., a multiple cloning site (MCS). The above-mentioned reporter genes were chosen because they can be readily assayed over a wide range of expression levels. For experimental controls, conventional monocistronic plasmids are also constructed that lack the RNA replicase gene but contain the same reporter genes flanked by the RNA2 cis-acting signals, placed directly downstream of an RNA pol II promoter. The levels and duration of reporter gene expression from the RNA replicon plasmids are compared with those from the control plasmids that rely solely on DNA-templated transcription for mRNA synthesis.

Mono- (control) or dicistronic plasmids are transfected into various cell lines, such as BHK21, BSC40, CHO, *Drosophila* SL1 or SL2, HeLa, or HeP2 cells. Reporter gene expression is monitored by measuring the accumulation of mRNA, protein, and enzyme activity. Rates of replication of the chimeric RNAs are measured by gel analysis of RNAs labeled metabolically, and the accumulated mRNA levels are determined by RT-PCR, Northern blotting, primer extension, and/or ribonuclease protection assays. Primary transcripts templated by the monocistronic plasmids in the absence of replication are quantitated by primer extension, and the levels compared with those resulting from replicative amplification. The relative rates of protein synthesis are measured by immunoprecipitation of [$^{35}$S]-methioninelabeled reporter proteins, and their accumulated levels determined by Western blot analysis of the proteins from transfected cells. Luciferase activity and GFP fluorescence are measured to determine the levels of correctly-folded, soluble, and functional reporter proteins. Typically in nodaviral-infected cells, the capsid protein precursor α accumulates to levels that can readily be detected by staining of SDS-polyacrylamide gels (23). Therefore, the reporter genes may also be monitored in a similar way.

EXAMPLE 10

Cultured Mammalian Cells Transfected With the Nodavirus-Based DNA Expression Vector To examine the influence that the promoter has on the ensuing level of RNA replication, the ability of other pol II promoters to launch RNA replication in other cell lines and cell types is investigated. The efficacy of the hormone-responsive promoter is compared with the strong constitutive promoter from the human cytomegalovirus (CMV) major immediate early gene (24, 25), and the constitutive SV40 and RSV promoters (20). These experiments determine whether the level or inducibility of primary transcription is critical for determining the resulting RNA replication activity. As with the previous constructs, the CMV promoter is positioned such that primary transcription initiates at the first nucleotide of RNA1, resulting in a promoter-cDNA junction with the following sequence (non-template strand):

5' . . . TAGTGAACCGGTATTGAATC . . . 3' (SEQ ID No. 5)

The CMV promoter is shown in normal font, while the 5' end of the NoV RNA1 cDNA is shown in bold font with the transcriptional start site, as determined by Boshart et al. (25), underlined. Dicistronic plasmids, such as that illustrated in FIG. 5, are used to compare the inducible and constitutive promoters and determine the level of RNA replication that each initiates. Plasmids that express inactive RNA replicase (10) or no replicase at all are used as controls to compare the levels of primary transcription from the different promoters.

Dicistronic reporter gene plasmids that contain either the CMV promoter, the SV40 or RSV constitutive promoters, or the hormone-inducible promoter are transfected into various cell lines, including the hormone-responsive CHO cells. The levels of luciferase mRNA are quantitated by primer extension analysis and densitometric scanning of the resulting autoradiographs to determine the exent of replication initiated by each plasmid. The level of primary transcription is determined by Northern blot analysis of nuclear, and cytoplasmic RNAs extracted from cells transfected with the control plasmids that express inactive RNA replicase or no RNA replicase at all.

EXAMPLE 11

Experiments in Mice

Matched pairs of reporter plasmids (with and without the RNA replicase gene) containing a constitutive promoter are introduced separately into the lungs of groups of 10 mice, using the lipid-mediated delivery conditions of Sorscher et al. (26). Reporter gene expression is measured following sacrifice of the animals and excision of their lungs. The effects of plasmid concentration and the longevity of reporter gene expression are examined.

EXAMPLE 12

Expression of a Therapeutic Heterologous Gene To determine whether mRNA encoding a therapeutic gene is replicated efficiently by the nodavirus replicase, a full-length cDNA encoding the cystic fibrosis transmembrane conductance regulator (CFTR) is incorporated downstream in a tandem replicon plasmid of the structure shown in FIG. 5. As before, a control plasmid that lacks the nodavirus replicase gene is also constructed and the two plasmids compared for their ability to express the cystic fibrosis transmembrane conductance regulator in transfected cells in culture. Assays for mRNA replication and translation are performed using CFTR-specific hybridization probes and antibodies. Additional experiments are performed to examine cystic fibrosis transmembrane conductance regulator mRNA replication and duration of gene expression in primary airway cells isolated from cystic fibrosis patients.

EXAMPLE 13

Cell Culture System to Produce Infectious Nodavirus

The experiments described herein also provide a method for the production of infectious NoV and PaV viruses for which no cell culture system currently exists (2, 23). By introducing DNAs that transcribe NoV or PaV RNAs into host cells, the corresponding infectious viruses are produced. The full-length, functional cDNA clones constructed herein provide this culturing capability for both NoV and for PaV.

Cultured baby hamster kidney cells that expressed bacteriophage T7 DNA-dependent RNA polymerase (T7 pol) were co-transfected with plasmids containing cDNAs of PaV RNAs 1 and 2, or mock transfected. Forty-eight hours post-transfection, the cells were lysed and whole-cell lysates were injected into the hemocoel of larvae of the greater wax-moth (*Galleria mellonella*) (16 larvae per group). Larval mortality and weights were recorded.

The results indicated that the lysate of plasmid-transfected cells arrested larval growth, as shown by the cessation of weight gain (FIG. 5B), and induced significant larval mortality 16 days post-injection (FIG. 5A). These effects were indistinguishable from those of authentic PaV. Hence, these results establish that infectious virus can be recovered from the cDNA clones whose sequences are described herein.

EXAMPLE 14

Identification of an Insect Cell Line Susceptible to Infection by PaV

A survey of more than a dozen insect cell lines revealed several that were susceptible to infection with PaV. From these, one cell-line (FB33) from the corn earworm (*Helicoverpa zea*) was chosen for further study.

FB33 cells were infected with authentic wild-type PaV or with virus recovered from the cDNA clones of PaV RNAs 1 and 2. The products of RNA replication were specifically labeled by metabolic incorporation of [$^3$H]uridine in the presence of actinomycin D. The labeled RNAs were resolved by electrophoresis on agarose-formaldehyde gels and visualized by fluorography.

As shown in FIG. 6, two major actinomycin D-resistant RNA species were detected in infected cells, with apparent sizes that corresponded to the genome segments of PaV RNA1 of about 3 kb and RNA2 of about 1.3 kb (lane 2). These RNAs were clearly visible above the background which consisted of three cellular RNAs (derived from ribosomal RNAs) that were not completely inhibited by actinomycin D under these conditions (FIG. 6, lane 1). Low levels of an RNA of the size expected for RNA3 were also detected (FIG. 6, lane 2). Treatment of the virus sample with antiserum to PaV before infection prevented infection as shown by the disappearance of labeled RNAs 1 and 2 (FIG. 6, lane 3).

A similar pattern of labeled RNAs was observed in FB33 cells infected with PaV recovered from the infectious cDNA clones (FIG. 6, lane 4), and in this case too, infectivity was mostly eliminated by treatment of the virus sample with anti-PaV antiserum (FIG. 6, lane 5). The residual, neutralization-resistant, infectivity in this sample was attributed to direct transfer of PaV RNA1 from the plasmid-transfected mammalian cells to the infected insect cells (data not shown).

These results establish that *H. zea* FB33 cells are susceptible to infection with PaV, and they confirm the conclusion from the larval infectivity studies (see FIG. 5) that the cDNA clones encode infectious RNA transcripts. Other studies (data not shown) have confirmed that infected FB33 cells produce amplified levels of infectious PaV, and can therefore be used to study all stages of virus replication in cell culture.

EXAMPLE 15

Three-Dimensional Structure of PaV

The three dimensional structures of the nodaviruses have yielded many important insights into virus assembly, structure, and disassembly (28). This has been due to the work of Dr. J. E. Johnson and his colleagues at the Scripps Research Institute. Therefore a collaboration was established with Dr. Johnson to see if more insights could be gleaned from the structure of PaV.

PaV was grown in wax-moth larvae, purified by velocity gradient sedimentation, and shipped to Dr. Johnson for structural studies by X-ray crystallography and cryo-electron microscopy. Dr. Liang Tang in Dr. Johnson's research group determined the structure of PaV by both these methods, with results that surpassed all our expectations.

Figure 7:
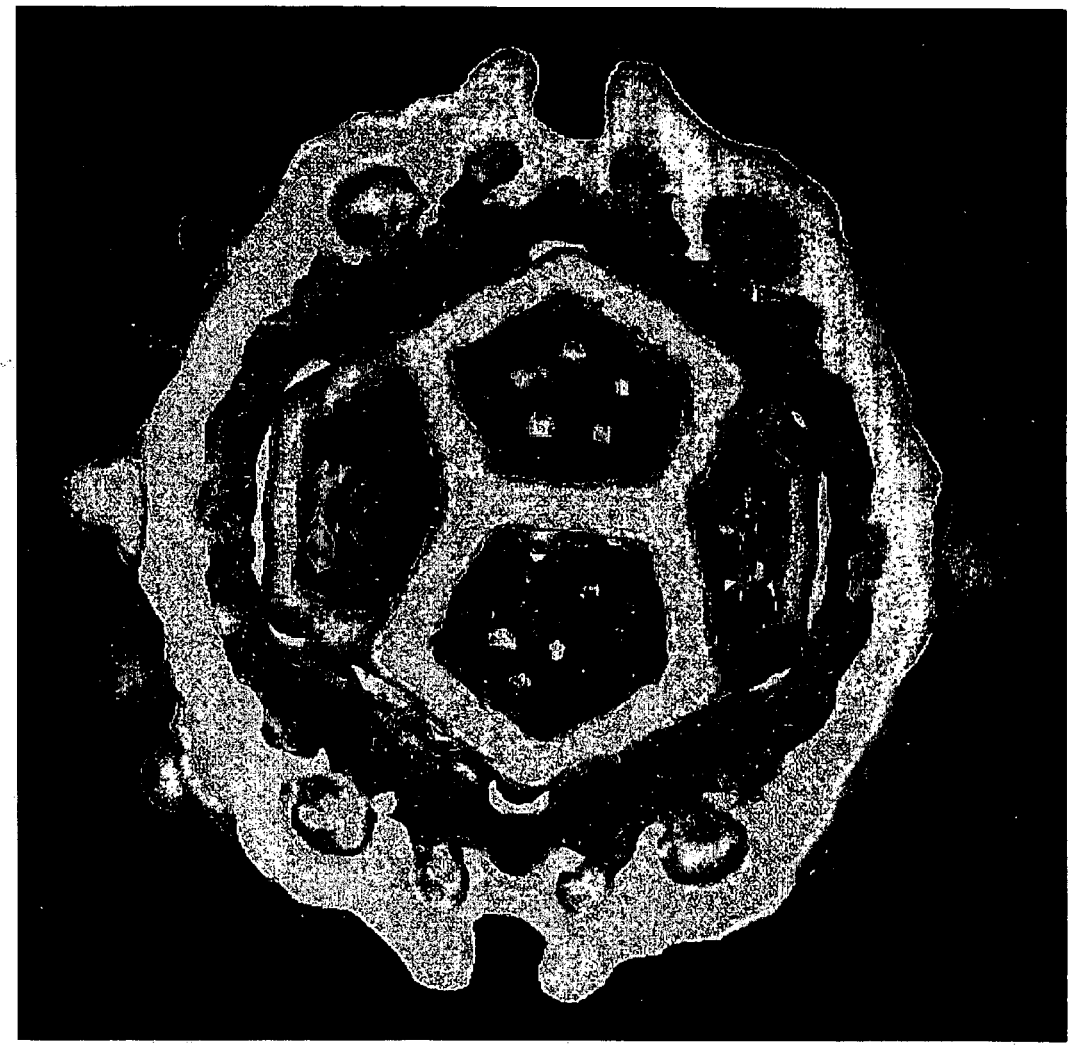
FIG. 7 shows the three-dimensional structure of PaV as revealed by cryo-electron microscopy and image reconstruction. In this image, the protein capsid (in gray) has been partly cut away to reveal the dodecahedral cage of duplex RNA (in yellow). The visible RNA in this figure represents about 40% of the total RNA in the virus particle.

For afficionados of nodavirus structure, there were several aspects of the results that were highly significant and enriched our prior understanding of these structures in general. But the most striking aspect of the results, and one which will be of major interest to non-specialists, is that for the first time with any spherical virus of this size, a major portion of the viral RNA is visible at high resolution (FIG. 7). The RNA that is visible at 3 Å resolution constitutes about 40% of the total RNA in the virus particle, some 1850 nucleotides. Unexpectedly, the visible RNA is arranged as a dodecahedral cage composed of thirty 26-base-pair RNA duplexes. The relationship between the nucleotide sequence of the viral RNAs (which do not contain even a single copy of a 26-nucleotide inverted repeat) and the three-dimensional RNA structure in virus particles is a subject of intense interest and speculation.

Small spherical virus particles have significant potential as systems for the specific encapsidation and delivery of biological and non-biological molecules. As this area of biotechnology progresses, knowledge of the internal structure of the capsid and the structural constraints that it imposes on the encapsidated contents will become increasingly important. At this point in time, PaV provides more high-resolution structural insights into the protein-RNA interactions th at drive virus assembly than any other system. Undoubtedly, the amino acid sequence of the PaV capsid protein is a major determinant of these interactions and it may therefore be valuable in the design of encapsidation systems with specificities that can be predicted and manipulated.

EXAMPLE 16

Activity of Nodamura Virus RNA Replicase in *Saccharomyces cerevisiae*

Figure 8:
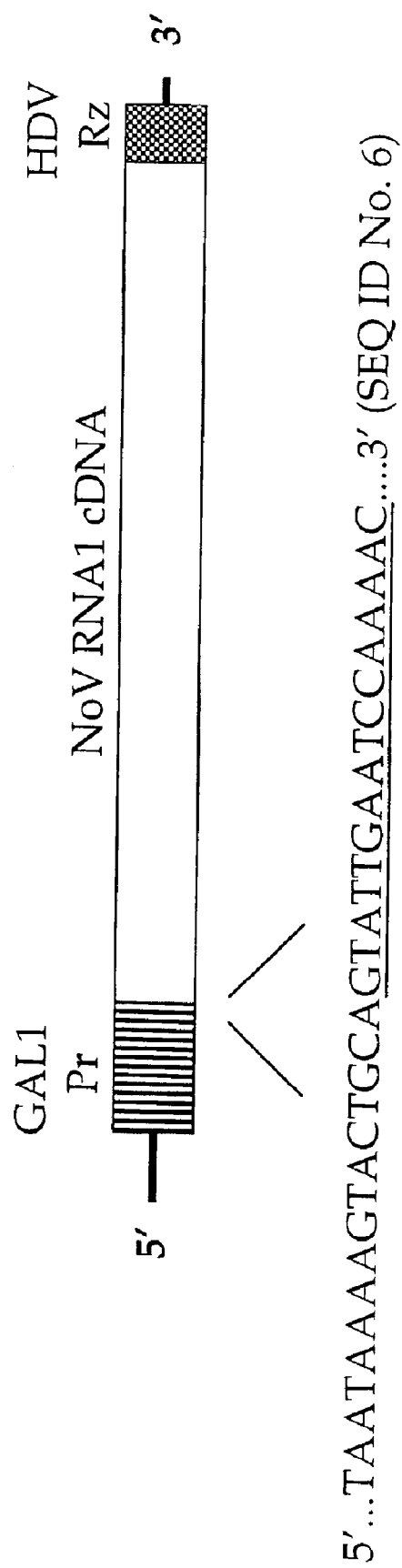
FIG. 8 shows the schematic diagram of yeast plasmid pN1 in which full-length NoV1 cDNA is flanked by the yeast GAL1 inducible promoter and the autolytic ribozyme of hepatitis delta virus (HDV Rz). The nucleotide sequence at the junction between the promoter and the NoV sequence (underlined) is shown.

Flock house virus (FHV), which is the best-studied of the nodaviruses, undergoes complete replication in the yeast *Saccharomyces cerevisiae* and produces high levels of infectious viral progeny (29). FHV is the only virus of a higher eukaryote that has been shown to replicate fully in yeast. In view of the convenience of yeast as an experimental organism, the power of its genetics, and its complete genome sequence, the recapitulation of all stages of the viral replication cycle is an important result that opens the way to technological exploitation in a variety of ways. Indeed, a patent has been awarded to protect aspects of the FHV/yeast system. Because of the potential of this system, the capacity of the cDNA clone of NoV RNA1 to synthesize a self-replicating RNA in *Saccharomyces cerevisiae* was examined.

cDNA representing the complete sequence of NoV RNA1 was inserted into a shuttle plasmid that could replicate in both *E. coli* and yeast. The cDNA was flanked on the upstream side by the inducible GAL1 promoter for RNA polymerase II, and on the downstream side by the hepatitis delta virus (HDV) ribozyme (Rz) as in our other constructs (FIG. 8) (see (30) for review). The plasmid was transformed into competent yeast cells and colonies containing the plasmid were selected by means of an auxotrophic marker. After induction of the promoter with galactose, total RNA was extracted from the cells, resolved by agarose-formaldehyde gel electrophoresis, and NoV-specific RNAs were detected by northern blotting using strand-specific RNA probes.

Figure 9A:
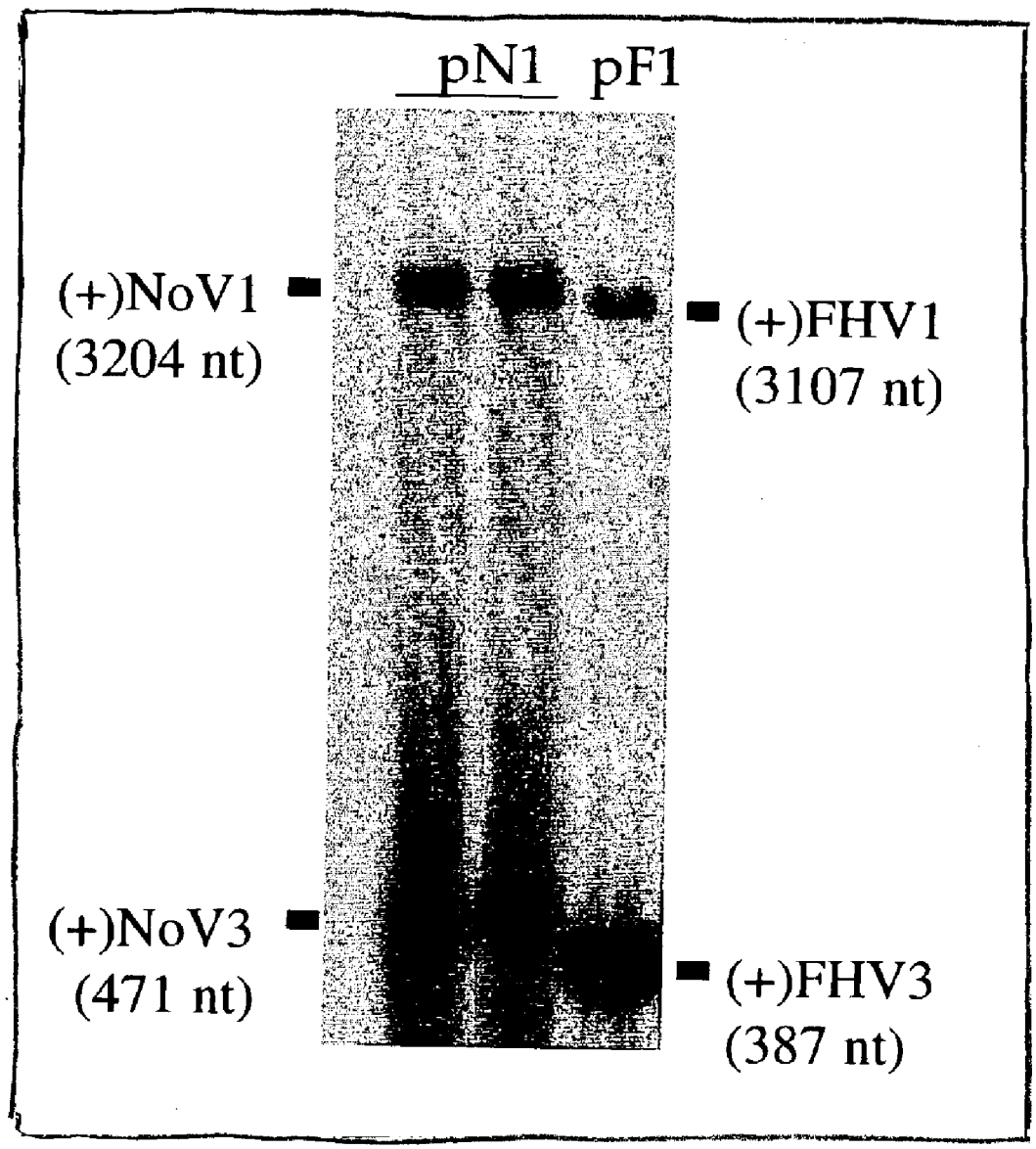
FIGS. 9A and 9B show the analysis of RNAs accumulating in yeast cells transformed with plasmid pNp1. Duplicate colonies of *Saccharomyces cerevisiae* cells containing pN1 were transferred to medium containing galactose to induce the pol II promoter, incubated for 24 hours, and total cellular RNAs were resolved by electrophoresis on denaturing agarose-formaldehyde gels. Viral RNAs were detected by probing northern transfers with RNA probes specific for positive-sense (FIG. 9A) or negative-sense (FIG. 9B) NoV or FHY RNA1. The visualized RNAs are identified by their sense, virus specificity, and nucleotide content beside the lanes.
Figure 9B:
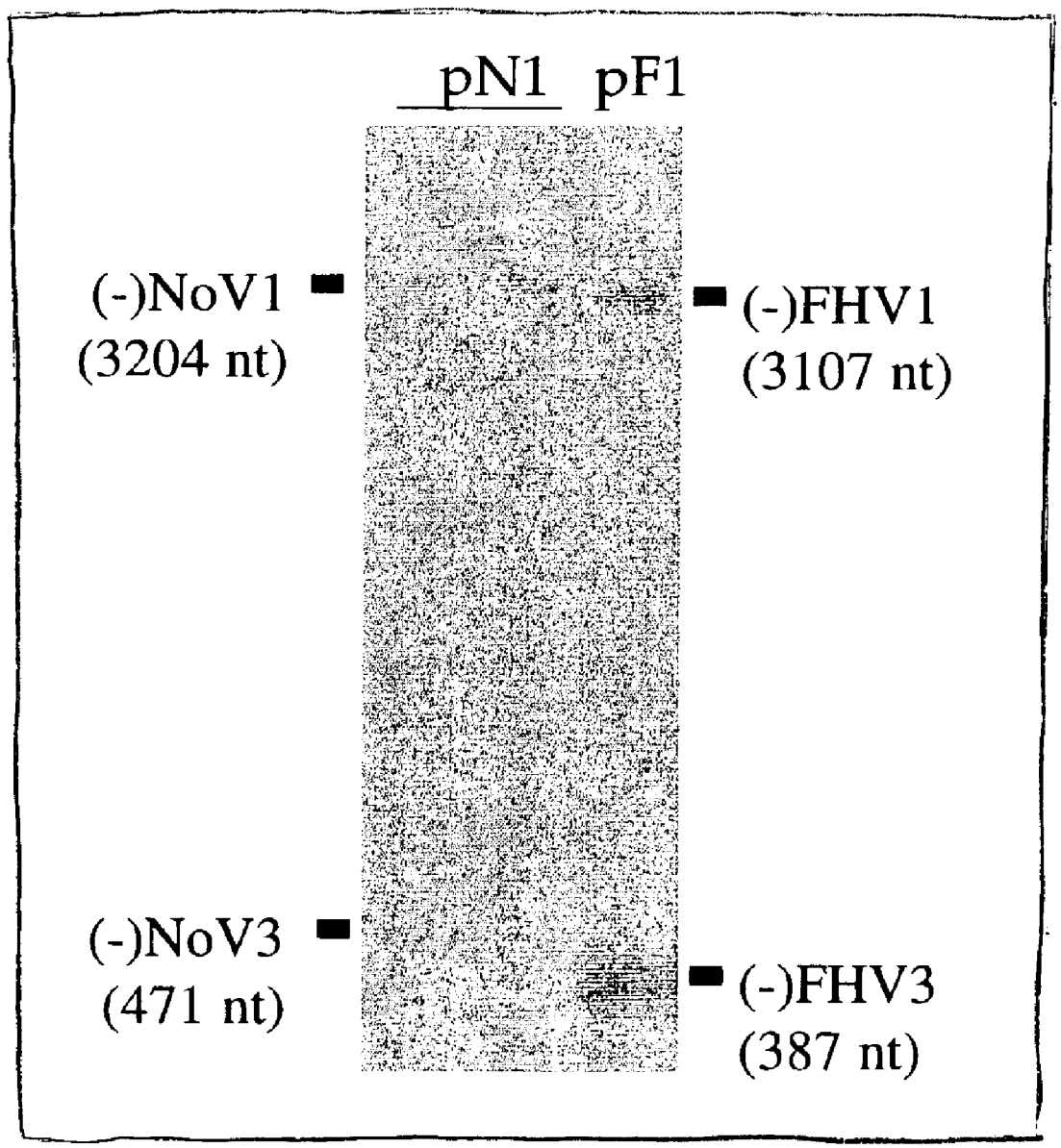

Two positive-sense NoV-specific RNAs were detected which comigrated with authentic NoV RNAs 1 and 3 (FIG. 9A). The presence of NoV RNA1 was to be expected because it would be transcribed by cellular pol II in a DNA-templated reaction, but the presence of RNA3 indicated that RNA replication was occurring since this subgenomic RNA species is produced only during RNA replication. The presence of negative-sense RNA1 confirmed RNA replication (FIG. 9B). The absence of negative-sense NoV RNA3 in FIG. 9B was attributable to the RNA probe used in this experiment which would not have detected RNA3. Although careful comparative quantitation remains to be done, it appears that NoV RNA replicates in yeast as abundantly as FHV RNA, or more so.

These results show that primary (DNA-templated) transcripts of NoV RNA1 replicate in *Saccaromyces cerevisiae*, making NoV only the third virus of a higher eukaryote for which this has been demonstrated (the others being the plant virus brome mosaic virus and FHV). This result shows not only that NoV RNA replicase is active in this very foreign intracellular environment, but also that any host cell factor(s) necessary for RNA replication can be substituted by components from yeast.

NoV is the only nodavirus known to cross naturally between insects and mammals. As a model system, this makes it closer than FHV to the RNA viruses that infect man. For this reason, NoV RNA replicase would be a better target than the FHV enzyme for the development of screens for inhibitors that might have potential as antiviral agents. Moreover, the greater thermostablity of the NoV RNA replicase gives it distinct advantages over the FHV enzyme in most aspects of its forseeable uses in yeast.

The following references were cited herein:
1. Hendry, D. 1991. Nodaviridae of invertebrates, In E. Kurstak (ed.) *Viruses of Invertebrates*, Marcel Dekker, New York. p. 227–276.
2. Ball, L. A., & Johnson, K. L. 1998. Nodaviruses of insects. In: L. K. Miller and L. A. Ball (eds.) *The Insect Viruses*, of H. Fraenkel-Conrat and R. Wagner (series eds.) The Viruses. Plenum Publishing Corp., N.Y., Chapter 8, pp. 225–267.
3. Gallagher, T. M., et al. 1983. J. Virol. 46: 481–489.
4. Guarino, L. A., et al. 1984. Virology 139: 199–203.

5. Hosur, M. V., et al. 1987. Prot. Str. Fctn. Genet. 2: 167–176.
6. Schneemann, A., et al. 1992. J. Virol. 66: 6728–6734.
7. Gallagher, T, & Rueckert, R. 1988. J. Virol. 62: 3399–3406.
8. Johnson, J. & Reddy, V. 1998. Structural studies of nodaviruses and tetraviruses. In L. Miller and L. Ball, (eds) *The Insect Viruses*, of H. Fraenkel-Conrat and R. Wagner (series eds.) *The Viruses*. Plenum Publishing Corp., N.Y., Chapter 7, pp. 171–223.
9. Harper, T. 1994. Ph.D. thesis. University of Wisconsin-Madison.
10. Ball, L. A. 1995. RNA1. J. Virol. 69, 720–727.
11. Dasmahapatra, et al. 1986. Proc. Natl. Acad. Sci. USA 83: 63–66.
12. Ball, L. A. 1992. J. Virol. 66, 2335–2345.
13. Ball, L. A., & Li, Y. 1993. J. Virol. 67, 3544–3551.
14. Ball, L. 1994. Proc. Natl. Acad. Sci. USA 91, 12443–12447.
15. Ball, L. A., et al. 1994. Arch. Virol. [suppl] 9, 407–416.
16. Pattnaik, A. K., et al. 1992. Cell 69, 1011–1020.
17. Li, Y., & Ball, L. A. 1993. J. Virol. 67, 3854–3860.
18. Zhong, W. 1993. Ph.D. thesis. University of Wisconsin-Madison.
19. Price, B. D., et al. 1996. Proc. Natl. Acad. Sci. USA 93: 9465–9470.
20. Johnson, K. L., & Ball, L. A. 1997 J. Virol. 71, 3233–3327.
21. Johnson, K. L., & Ball, L. A. 1999. J. Virol., in press.
22. No, D., et al. 1996. Proc. Natl. Acad. Sci. USA. 93: 3346–3351.
23. Ball, L. A., et al. 1992. J. Virol. 66, 2326–2334.
24. Stenberg, R. M., et al. 1984. J. Virol. 49:190–199.
25. Boshart, M., et al. 1985. Cell 41:521–530.
26. Sorscher, E. J. et al. 1994. Human Gene Therapy 5: 1259–1277.
27. Dasgupta, R. & Sgro, J-Y. 1989. Nucleic Acids Res. 17:7525–6.
28. Schneemann et al. 1998. Adv. Virus Res. 50:381–446.
29. Price et al. 1996. Proc. Natl. Acad. Sci. USA. 93: 9465–9469.
30. Ball and Johnson. 1999. Adv. Virus Res. 53:229–243.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

|---|---|

What is claimed is:

1. An isolated cDNA encoding a Nodamura virus RNA2 genome segment and having the sequence shown in SEQ ID No. 2.

2. A DNA vector comprising the Nodamura virus cDNA of claim 1.

3. A host cell transfected with the DNA vector of claim 2.

4. An isolated cDNA encoding a Pariacoto virus RNA1 genome segment and having the sequence shown in SEQ ID No. 3.

5. A DNA vector comprising the Pariacoto virus cDNA of claim 4.

6. A host cell transfected with the DNA vector of claim 5.

7. An isolated cDNA encoding a Pariacoto virus RNA2 genome segment and having the sequence shown in SEQ ID No. 4.

8. A DNA vector comprising the Pariacoto virus cDNA of claim 7.

9. A host cell transfected with the DNA vector of claim 8.

10. A nodavirus-based DNA expression vector, wherein said expression vector comprises:
   i) a DNA-dependent RNA polymerase promoter operably linked to a cDNA encoding a nodavirus RNA-dependent RNA polymerase (RNA replicase), wherein said nodavirus is selected from the group consisting of flock house virus, Nodamura virus, and Pariacoto virus
   ii) a heterologous gene inserted at the 5' end of a cDNA encoding a nodavirus RNA2 transcript, wherein said nodavirus is selected from the group consisting of flock house virus Nodamura virus, and Pariacoto virus; and
   iii) a cDNA encoding a ribozyme, wherein upon transcription of said expression vector, said ribozyme cleaves the transcripts of said expression vector and generates a 3' end recognized by said RNA replicase, and wherein said recognition results in replication of said transcripts.

11. The expression vector of claim 10, wherein said ribozyme is from a hepatitis delta virus.

12. The expression vector of claim 10, wherein said DNA-dependent RNA polymerase promoter is selected from the group consisting of an inducible promoter, a constitutive promoter, a tissue-specific promoter and a synthetic promoter.

13. The expression vector of claim 10, wherein said nodavirus RNA replicase is encoded by a cDNA having the sequence of SED ID NO: 1 or 3.

14. The expression vector of claim 10, wherein said nodaviruis RNA2 transcript is encoded by a cDNA having the sequence of SEQ ID NO: 2 or 4.

15. The expression vector of claim 10, wherein said heterologous gene is selected from the group consisting of a gene encoding a desired protein, a gene encoding a ribozyme, a sequence encoding an antisense RNA, a gene encoding a therapeutic protein, a gene encoding the cystic fibrosis transmembrane conductance regulator, a gene encoding the herpes simplex virus thymidine kinase, a gene encoding a polynucleotide phosphorylase, a gene encoding alpha-globin and a gene encoding beta-globin.

16. The expression vector of claim 10, further comprising: eukaryotic poly(A) or transcriptional termination signals.

17. The expression vector of claim 10, further comprising a sequence that signals transcriptional termination by bacteriophage T7 RNA polymerase.

18. A method of replicative amplification of a transcript encoded by a nodavirus-based DNA expression vector in a cell, comprising the step of:
   introducing into a cell a nodavirus-based DNA expression vector of claim 10, or a RNA transcript of said vector, wherein the expression of RNA replicase encoded by said expression vector leads to amplification of transcripts encoded by said expression vector.

19. The expression vector of claim 12, wherein said inducible promoter is selected from the group consisting of a hormone-responsive Hsp70 promoter, a metallothionein promoter, an alcohol dehydrogenase promoter and a galactose promoter.

20. The expression vector of claim 12, wherein said constitutive promoter is selected from the group consisting of Rous sarcoma virus (RSV) LTR promoter, human cytomegalovirus (CMV) major immediate early gene promoter, SV40 early promoter and the beta-actin promoter.

21. The expression vector of claim 12, wherein said tissue-specific promoter is selected from the group consisting of an alpha-globin promoter and a beta-globin promoter.

22. The method of claim 18, wherein said introduction is by means selected from the group consisting of transfection, infection and injection.

23. The method of claim 18, wherein said introduction is selected from the group consisting of in vitro, in vivo, ex vivo and in situ.

24. The method of claim 18, wherein said cell is a tumor cell.

25. The method of claim 18, wherein said expression vector further comprises eukaryotic poly(A) or transcriptional termination signals.

26. The method of claim 18, wherein said expression vector further comprises a sequence that signals transcriptional termination by the bacteriophage T7 RNA polymerase.

27. The method of claim 22, wherein said infection is by an organism with a DNA genome into which the expression vector of claim 13 have been inserted.

28. The method of claim 27, wherein said organism is selected from the group consisting of adenovirus, herpesvirus, parvovirus, baculovirus, and papovavirus.

* * * * *

UNITED STATES PATENT AND TRADEMARK OFFICE
CERTIFICATE OF CORRECTION

PATENT NO. : 6,869,780 B2
DATED : March 22, 2005
INVENTOR(S) : Laurence A. Ball et al.

It is certified that error appears in the above-identified patent and that said Letters Patent is hereby corrected as shown below:

Title page,
Item [75], Inventors, "Karen" should read -- Karyn --.

Signed and Sealed this

Fourteenth Day of June, 2005

JON W. DUDAS
*Director of the United States Patent and Trademark Office*